US012622786B2

(12) United States Patent
Casey et al.

(10) Patent No.: US 12,622,786 B2
(45) Date of Patent: May 12, 2026

(54) PATIENT-SPECIFIC IMPLANT DESIGN, MANUFACTURE AND PLATFORM WITH CLINICAL AND THIRD-PARTY DATA ACQUISITION

(71) Applicant: Carlsmed, Inc., Carlsbad, CA (US)

(72) Inventors: Niall Patrick Casey, Carlsbad, CA (US); Sarah Jauregui, San Diego, CA (US); Jeremy Winston, San Diego, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 19/231,241

(22) Filed: Jun. 6, 2025

(65) Prior Publication Data

US 2025/0375298 A1     Dec. 11, 2025

Related U.S. Application Data

(60) Provisional application No. 63/657,725, filed on Jun. 7, 2024.

(51) Int. Cl.
 A61F 2/30 (2006.01)
 A61B 17/70 (2006.01)
  (Continued)

(52) U.S. Cl.
 CPC ...... A61F 2/30942 (2013.01); A61B 17/7002 (2013.01); A61B 34/10 (2016.02);
  (Continued)

(58) Field of Classification Search
 CPC ........ A61F 2/30; A61F 2/30942; G06T 15/00; G06F 30/10; G06H 20/40; G16H 30/20
 See application file for complete search history.

(56) References Cited

U.S. PATENT DOCUMENTS 4,704,686 A   11/1987  Aldinger
4,936,862 A    6/1990  Walker et al.
      (Continued)

FOREIGN PATENT DOCUMENTS

CN   104318009 A   1/2015
CN   104353121 A   2/2015
      (Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Christopher J Beccia

(74) *Attorney, Agent, or Firm* — Perkins Coie LLP

(57) ABSTRACT

Systems and methods for designing patient-specific orthopedic implants. The systems and methods can include automated collection protocols for available third-party data to use to generate surgical plans or patient-specific orthopedic implant designs. The system can identify triggers for collecting third-party data. The system can determine a confidence score for the collected third-party data based on the type of data, the source of the data, and the similarity of the data to patient data. The system can select parameters in the third-party data to integrate into designing a patient-specific implant or patient treatment.

29 Claims, 22 Drawing Sheets

(51) Int. Cl.

| | |
|---|---|
| *A61B 34/10* | (2016.01) |
| *A61F 2/44* | (2006.01) |
| *G06Q 50/04* | (2012.01) |
| *G16H 10/60* | (2018.01) |
| *G16H 20/40* | (2018.01) |
| *A61B 17/00* | (2006.01) |

(52) U.S. Cl.

CPC ........ *A61F 2/30749* (2013.01); *A61F 2/4455* (2013.01); *G06Q 50/04* (2013.01); *G16H 10/60* (2018.01); *G16H 20/40* (2018.01); *A61B 2017/00526* (2013.01); *A61B 2034/104* (2016.02); *A61B 2034/105* (2016.02); *A61B 2034/108* (2016.02); *A61F 2002/30952* (2013.01); *A61F 2002/30953* (2013.01); *A61F 2002/30963* (2013.01)

(56) References Cited

U.S. PATENT DOCUMENTS

| | | | |
|---|---|---|---|
| 5,431,562 A | 7/1995 | Andreiko et al. |
| D420,995 S | 2/2000 | Imamura et al. |
| D436,580 S | 1/2001 | Navano et al. |
| 6,315,553 B1 | 11/2001 | Sachdeva et al. |
| 6,540,512 B1 | 4/2003 | Sachdeva et al. |
| 6,696,073 B2 | 2/2004 | Boyce et al. |
| 6,772,026 B2 | 8/2004 | Bradbury et al. |
| 6,932,842 B1 | 8/2005 | Litschko et al. |
| 6,978,188 B1 | 12/2005 | Christensen |
| 6,988,241 B1 | 1/2006 | Guttman et al. |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano et al. |
| 7,747,305 B2 | 6/2010 | Dean et al. |
| 7,756,314 B2 | 7/2010 | Karau et al. |
| 7,799,077 B2 | 9/2010 | Lang et al. |
| D633,514 S | 3/2011 | Tokunaga et al. |
| D656,153 S | 3/2012 | Imamura et al. |
| 8,246,680 B2 | 8/2012 | Betz et al. |
| 8,265,949 B2 | 9/2012 | Haddad |
| 8,275,594 B2 | 9/2012 | Lin et al. |
| 8,337,507 B2 | 12/2012 | Lang et al. |
| 8,394,142 B2 | 3/2013 | Bertagnoli et al. |
| 8,457,930 B2 | 6/2013 | Schroeder |
| 8,532,806 B1 | 9/2013 | Masson |
| 8,556,983 B2 | 10/2013 | Steines et al. |
| 8,644,568 B1 | 2/2014 | Hoffmann et al. |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean et al. |
| 8,843,229 B2 | 9/2014 | Vanasse et al. |
| 8,855,389 B1 | 10/2014 | Hoffmann et al. |
| 8,870,889 B2 | 10/2014 | Frey |
| 9,020,788 B2 | 4/2015 | Lang et al. |
| D735,231 S | 7/2015 | Omiya |
| D737,309 S | 8/2015 | Kito et al. |
| 9,198,678 B2 | 12/2015 | Frey et al. |
| 9,208,558 B2 | 12/2015 | Dean et al. |
| D757,025 S | 5/2016 | Kim et al. |
| D761,842 S | 7/2016 | Johnson et al. |
| 9,411,939 B2 | 8/2016 | Furrer et al. |
| 9,445,907 B2 | 9/2016 | Meridew et al. |
| 9,452,050 B2 | 9/2016 | Miles et al. |
| D774,076 S | 12/2016 | Fuller et al. |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett et al. |
| 9,715,563 B1 | 7/2017 | Schroeder |
| D797,760 S | 9/2017 | Tsujimura et al. |
| D797,766 S | 9/2017 | Ibsies |
| D798,312 S | 9/2017 | Tsujimura et al. |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado et al. |
| 9,993,341 B2 | 6/2018 | Vanasse et al. |
| 10,034,676 B2 | 7/2018 | Donner |
| D825,605 S | 8/2018 | Jann et al. |
| D826,977 S | 8/2018 | Nakajima et al. |
| 10,089,413 B2 | 10/2018 | Wirx-Speetjens et al. |
| D841,675 S | 2/2019 | Hoffman et al. |
| 10,213,311 B2 | 2/2019 | Mahfouz |
| D845,973 S | 4/2019 | Jaycobs |
| D845,974 S | 4/2019 | Cooperman et al. |
| D847,165 S | 4/2019 | Kolbenheyer |
| D848,468 S | 5/2019 | Ng et al. |
| D849,029 S | 5/2019 | Cooperman et al. |
| D849,773 S | 5/2019 | Jiang et al. |
| 10,292,770 B2 | 5/2019 | Ryan et al. |
| 10,299,863 B2 | 5/2019 | Grbic et al. |
| D854,560 S | 7/2019 | Field et al. |
| D854,561 S | 7/2019 | Field et al. |
| 10,390,958 B2 | 8/2019 | Maclennan |
| D860,237 S | 9/2019 | Li et al. |
| D860,238 S | 9/2019 | Bhardwaj et al. |
| D866,577 S | 11/2019 | Eisert et al. |
| D867,379 S | 11/2019 | Ang |
| D867,389 S | 11/2019 | Jamison et al. |
| 10,463,433 B2 | 11/2019 | Turner et al. |
| D870,762 S | 12/2019 | Mendoza Corominas et al. |
| 10,512,546 B2 | 12/2019 | Kamer et al. |
| 10,517,681 B2 | 12/2019 | Roh et al. |
| D872,117 S | 1/2020 | Kobayashi et al. |
| D872,756 S | 1/2020 | Howell et al. |
| D874,490 S | 2/2020 | Dodsworth |
| D875,761 S | 2/2020 | Heffernan et al. |
| D876,454 S | 2/2020 | Knowles et al. |
| D876,462 S | 2/2020 | Li et al. |
| D877,167 S | 3/2020 | Knowles et al. |
| D879,112 S | 3/2020 | Hejazi et al. |
| 10,588,589 B2 | 3/2020 | Bregman-Amitai et al. |
| 10,603,055 B2 | 3/2020 | Donner et al. |
| D880,513 S | 4/2020 | Wang et al. |
| D881,908 S | 4/2020 | Sunil et al. |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel et al. |
| D896,828 S | 9/2020 | Linares et al. |
| D898,054 S | 10/2020 | Everhart et al. |
| D899,438 S | 10/2020 | Crafts et al. |
| 10,806,597 B2 | 10/2020 | Sournac et al. |
| 10,902,944 B1 | 1/2021 | Casey et al. |
| D916,868 S | 4/2021 | Evangeliou et al. |
| D916,879 S | 4/2021 | Mitsumori et al. |
| D918,253 S | 5/2021 | Choe et al. |
| 11,000,334 B1 | 5/2021 | Young et al. |
| D921,675 S | 6/2021 | Kmak et al. |
| D921,677 S | 6/2021 | Kmak et al. |
| D921,687 S | 6/2021 | Kmak et al. |
| D924,909 S | 7/2021 | Nasu et al. |
| D925,567 S | 7/2021 | Hayamizu |
| D927,528 S | 8/2021 | Heisler et al. |
| 11,083,586 B2 | 8/2021 | Cordonnier |
| 11,112,770 B2 | 9/2021 | Roh et al. |
| D933,692 S | 10/2021 | Smith et al. |
| 11,166,764 B2 | 11/2021 | Roh et al. |
| 11,185,369 B2 | 11/2021 | Ryan et al. |
| D937,870 S | 12/2021 | Pinto et al. |
| D937,876 S | 12/2021 | Harvey |
| D938,461 S | 12/2021 | Hoffman et al. |
| D938,986 S | 12/2021 | Grossberg |
| D940,178 S | 1/2022 | Ang |
| D946,022 S | 3/2022 | Nuttbrown et al. |

(56) References Cited

U.S. PATENT DOCUMENTS

| | | |
|---|---|---|
| D946,023 S | 3/2022 | Nuttbrown et al. |
| D946,024 S | 3/2022 | Vogler-Ivashchanka et al. |
| D946,616 S | 3/2022 | Tsai et al. |
| D958,151 S | 7/2022 | Casey |
| 11,376,076 B2 | 7/2022 | Casey et al. |
| 11,432,943 B2 | 9/2022 | Casey et al. |
| 11,439,514 B2 | 9/2022 | Casey et al. |
| 11,497,559 B1 | 11/2022 | Roh et al. |
| 2004/0104512 A1 | 6/2004 | Eidenschink |
| 2005/0234555 A1 | 10/2005 | Sutton et al. |
| 2005/0273170 A1 | 12/2005 | Navarro et al. |
| 2006/0100497 A1 | 5/2006 | Sawazaki et al. |
| 2007/0272747 A1 | 11/2007 | Woods et al. |
| 2007/0276369 A1 | 11/2007 | Allard et al. |
| 2007/0276501 A1* | 11/2007 | Betz .................... A61F 2/30942 |
| | | 264/222 |
| 2008/0227047 A1 | 9/2008 | Lowe et al. |
| 2009/0062739 A1 | 3/2009 | Anderson |
| 2010/0145734 A1 | 6/2010 | Becerra et al. |
| 2010/0191088 A1 | 7/2010 | Anderson et al. |
| 2010/0324692 A1 | 12/2010 | Uthgenannt et al. |
| 2011/0196451 A1 | 8/2011 | Hill |
| 2012/0150243 A9 | 6/2012 | Crawford et al. |
| 2012/0322018 A1 | 12/2012 | Lowe et al. |
| 2013/0323669 A1 | 12/2013 | Lowe |
| 2014/0072608 A1 | 3/2014 | Logothetidis et al. |
| 2014/0074438 A1 | 3/2014 | Furrer et al. |
| 2014/0081659 A1 | 3/2014 | Nawana et al. |
| 2014/0086780 A1 | 3/2014 | Miller et al. |
| 2014/0100886 A1 | 4/2014 | Woods et al. |
| 2014/0164022 A1 | 6/2014 | Reed et al. |
| 2014/0263674 A1 | 9/2014 | Cerveny |
| 2014/0277487 A1 | 9/2014 | Davenport et al. |
| 2014/0350614 A1 | 11/2014 | Frey et al. |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk et al. |
| 2015/0213225 A1 | 7/2015 | Amarasingham et al. |
| 2015/0324490 A1 | 11/2015 | Page |
| 2015/0328004 A1 | 11/2015 | Mafhouz |
| 2015/0332018 A1 | 11/2015 | Rosen et al. |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia et al. |
| 2016/0081810 A1 | 3/2016 | Reiley et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto et al. |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354213 A1 | 12/2016 | Cowan |
| 2016/0378919 A1 | 12/2016 | Mcnutt et al. |
| 2017/0000566 A1 | 1/2017 | Gordon et al. |
| 2017/0014169 A1 | 1/2017 | Dean et al. |
| 2017/0020679 A1 | 1/2017 | Maclennan |
| 2017/0035514 A1 | 2/2017 | Fox et al. |
| 2017/0061375 A1 | 3/2017 | Laster et al. |
| 2017/0068792 A1 | 3/2017 | Reiner |
| 2017/0112548 A1 | 4/2017 | Alamin et al. |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0196499 A1 | 7/2017 | Hunter |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Van et al. |
| 2017/0340447 A1 | 11/2017 | Mahfouz |
| 2017/0354510 A1 | 12/2017 | O'neil et al. |
| 2017/0367645 A1 | 12/2017 | Klinder et al. |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold et al. |
| 2018/0168731 A1 | 6/2018 | Reid et al. |
| 2018/0185075 A1 | 7/2018 | She |
| 2018/0233222 A1 | 8/2018 | Daley et al. |
| 2018/0233225 A1 | 8/2018 | Experton et al. |
| 2018/0250075 A1 | 9/2018 | Cho |
| 2018/0303552 A1* | 10/2018 | Ryan .................. A61B 17/7002 |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0065685 A1 | 2/2019 | Pickover et al. |
| 2019/0069956 A1 | 3/2019 | Ryan et al. |
| 2019/0099221 A1 | 4/2019 | Schmidt et al. |
| 2019/0201106 A1 | 7/2019 | Siemionow et al. |
| 2019/0262084 A1 | 8/2019 | Roh et al. |
| 2019/0266597 A1 | 8/2019 | Mohtar |
| 2019/0290361 A1* | 9/2019 | Shalayev ............... A61B 34/10 |
| 2019/0328929 A1 | 10/2019 | Kugler et al. |
| 2019/0333622 A1 | 10/2019 | Levin et al. |
| 2019/0354693 A1 | 11/2019 | Yoon et al. |
| 2019/0380792 A1 | 12/2019 | Poltaretskyi et al. |
| 2019/0388131 A1 | 12/2019 | Mehl et al. |
| 2020/0021570 A1 | 1/2020 | Lin |
| 2020/0078180 A1 | 3/2020 | Casey |
| 2020/0085509 A1 | 3/2020 | Roh et al. |
| 2020/0170802 A1 | 6/2020 | Casey |
| 2020/0258605 A1 | 8/2020 | Blechman |
| 2020/0261156 A1 | 8/2020 | Schmidt et al. |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Bálint |
| 2021/0145519 A1 | 5/2021 | Mosnier et al. |
| 2021/0169576 A1 | 6/2021 | Yoshinaka et al. |
| 2021/0192759 A1 | 6/2021 | Lang |
| 2021/0210189 A1 | 7/2021 | Casey et al. |
| 2021/0287770 A1 | 9/2021 | Anderson et al. |
| 2021/0378752 A1 | 12/2021 | Paul et al. |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0370142 A1 | 11/2022 | Schoenefeld et al. |
| 2022/0387191 A1 | 12/2022 | Cordonnier |
| 2022/0401150 A1 | 12/2022 | Cordonnier et al. |
| 2022/0406452 A1 | 12/2022 | Shelton |
| 2022/0409140 A1 | 12/2022 | Cordonnier et al. |
| 2023/0000560 A1 | 1/2023 | Roh et al. |
| 2023/0014384 A1 | 1/2023 | Cordonnier et al. |
| 2023/0023440 A1 | 1/2023 | Casey et al. |
| 2023/0034731 A1 | 2/2023 | Cordonnier et al. |
| 2023/0052263 A1 | 2/2023 | Casey et al. |
| 2023/0138162 A1 | 5/2023 | Winston et al. |
| 2024/0065767 A1 | 2/2024 | Cordonnier et al. |
| 2024/0225844 A1 | 7/2024 | Casey et al. |
| 2024/0307120 A1 | 9/2024 | Casey et al. |
| 2024/0428954 A1 | 12/2024 | Casey |
| 2025/0107897 A1 | 4/2025 | Winston |

FOREIGN PATENT DOCUMENTS

| | | |
|---|---|---|
| CN | 204468348 U | 7/2015 |
| CN | 105796214 A | 7/2016 |
| CN | 106202861 A | 12/2016 |
| CN | 107220933 A | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 A | 11/2021 |
| EP | 3120796 A1 | 1/2017 |

(56) References Cited

FOREIGN PATENT DOCUMENTS

| EP | 3954338 | A1 | 2/2022 |
|----|---------|-----|---------|
| WO | 9507509 | A1 | 3/1995 |
| WO | 2004110309 | A2 | 12/2004 |
| WO | 2010151564 | A1 | 12/2010 |
| WO | 2012154534 | A1 | 11/2012 |
| WO | 2014180972 | A2 | 11/2014 |
| WO | 2016172694 | A1 | 10/2016 |
| WO | 2017116346 | A1 | 7/2017 |
| WO | 2019112917 | A1 | 6/2019 |
| WO | 2019148154 | A1 | 8/2019 |
| WO | 2019165152 | A1 | 8/2019 |
| WO | 2019241167 | A1 | 12/2019 |
| WO | 2020033743 | A1 | 2/2020 |
| WO | 2020055874 | A1 | 3/2020 |
| WO | 2021141849 | A1 | 7/2021 |
| WO | 2022045956 | A1 | 3/2022 |
| WO | 2022192222 | A1 | 9/2022 |
| WO | 2023034405 | A1 | 3/2023 |

OTHER PUBLICATIONS

International Search Report and Written Opinion for International Patent Application No. PCT/US22/48536, mailed Apr. 13, 2023, 12 pages.

International Search Report and Written Opinion for International Patent Application No. PCT/US24/10934, mailed May 17, 2024, 28 pages.

International Search Report and Written Opinion for International Patent Application No. PCT/US24/109760, mailed Jul. 26, 2024, 18 pages.

International Search Report and Written Opinion for International Patent Application No. PCT/US24/35310, mailed Nov. 14, 2024, 16 pages.

Mandel et al., "Image-Guided Tethering Spine Surgery With Outcome Prediction Using Spatio-Temporal Dynamic Networks." IEEE Transactions on Medical Imaging, vol. 40, Issue 2, Feb. 2021, 12 pages.

Materialise Mimics, "Efficiently turn scans into accurate virtual 3D models," Retrieved on Nov. 1, 2019 at www.materialize.com/en/medical/software/mimics, 1 page.

Pimenta, Dr. Luiz, "Current Surgical Strategies to Restore Proper Sagittal Alignment," Journal of Spine 2015, vol. 4, Issue 4, 2 pages.

Fernandes, et al. Evaluation of the contact surface between vertebral endplate and 3D printed patient-specific cage vs commercial cage. Sci Rep 12, 12505 (2022). https://doi.org/10.1038/s41598-022-16895-9; 8 pages.

International Search Report and Written Opinion for International Patent Application No. PCT/US25/32769, mailed Aug. 19, 2025, 26 pages.

* cited by examiner

200

400

| PATIENT | |
|---|---|
| PT. ID | JDoe |
| Metric | Value |
| Age | 58 |
| Gender | M |
| BMI | 32 |
| LL | 40 |
| PI | 55 |
| Levels | 4 |

600

602
Detect trigger to collect third-party data

604
Collect the third-party data

606
Determine confidence score of the third-party data

620

Obtain third-party data for implant parameters — 622

Integrate the third-party data parameters into implant design database — 624

Determine implant dimension and surface parameters — 626

Train machine learning model — 628

640

Identify and format third-party data for database   642

Compare third-party data to patient data   644

Integrate with acquired patient data   646

Curate databases tagged with third-party data   648

Notify patient and/or healthcare provider   650

700
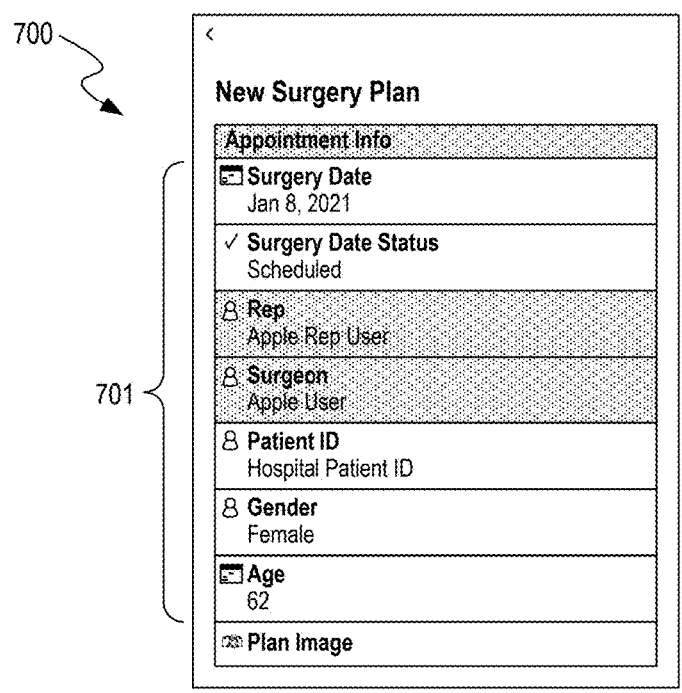
701
FIG. 7A
700
701
702
FIG. 7B
700
702
FIG. 7C
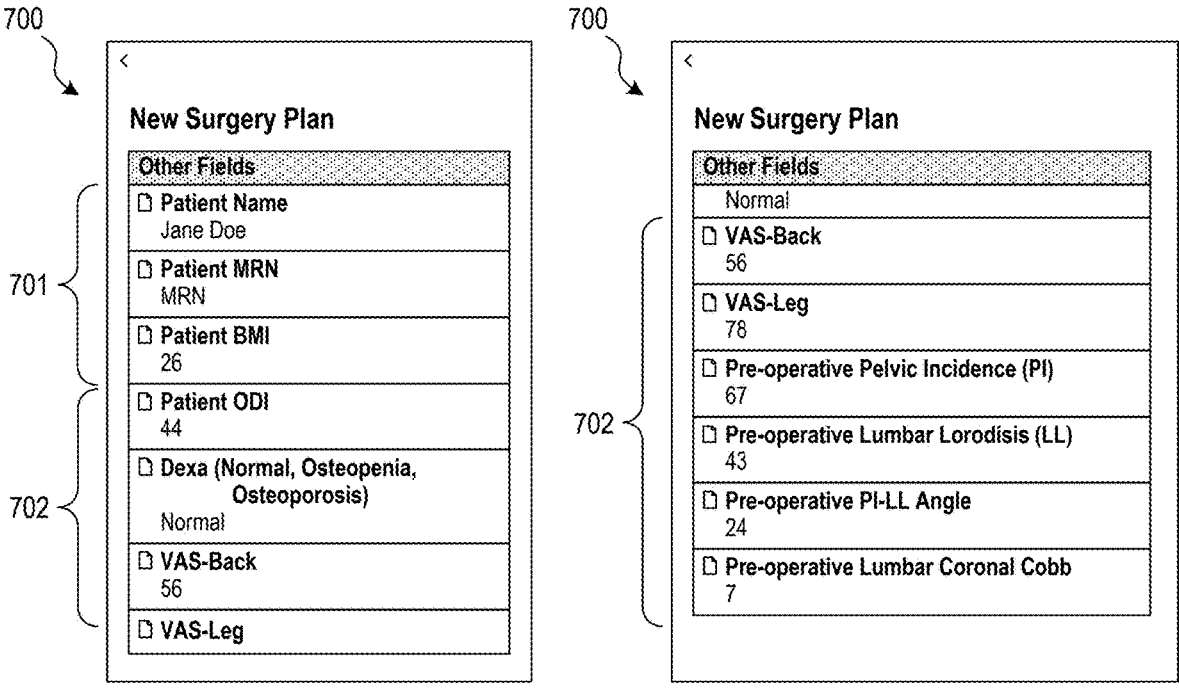

800

L4

L3

L2

L1

Sacrum

PATIENT-SPECIFIC IMPLANT DESIGN, MANUFACTURE AND PLATFORM WITH CLINICAL AND THIRD-PARTY DATA ACQUISITION

CROSS-REFERENCE TO RELATED APPLICATION

This application is a non-provisional of and claims priority to U.S. Provisional Patent Application No. 63/657,725, filed Jun. 7, 2024 entitled "PATIENT-SPECIFIC IMPLANT DESIGN AND PLATFORM WITH CLINICAL DATA ACQUISITION," which is hereby incorporated by reference in its entirety for all purposes.

TECHNICAL FIELD

The present disclosure is generally related to designing, manufacturing, and implementing medical care, and more particularly to systems and methods for designing and manufacturing patient-specific implants.

BACKGROUND

Numerous types of data associated with patient treatments and surgical interventions are available. To determine treatment protocols for a patient, physicians often rely on a subset of patient data available via the patient's medical record and historical outcome data. However, the amount of patient data and historical data may be limited, and the available data may not be correlated or relevant to the particular patient to be treated. Conventional technologies in the field of orthopedics may lack the capability to draw upon large data sets to generate and optimize patient-specific treatments (e.g., surgical interventions and/or implant designs) to achieve favorable treatment outcomes. Unfortunately, during a patient-specific treatment there is no current way to actively collect and analyze third-party data related to the patient.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 4A illustrates a patient data set. FIG. 4B illustrates a plurality of reference patient data sets. FIG. 4C illustrates similarity scores and outcome scores for the reference patient data sets of FIG. 4B.

FIGS. 7A-7D illustrate an exemplary patient data set that may be used and/or generated in connection with the methods described herein, according to an embodiment.

FIGS. 9A-1-9B-2 illustrate an exemplary virtual model of a patient's spine in a pre-operative anatomical configuration and a corrected anatomical configuration. More specifically, FIGS. 9A-1 and 9A-2 illustrate the pre-operative anatomical configuration of the patient, and FIGS. 9B-1 and 9B-2 illustrate the corrected anatomical configuration.

DETAILED DESCRIPTION

Figure 1:
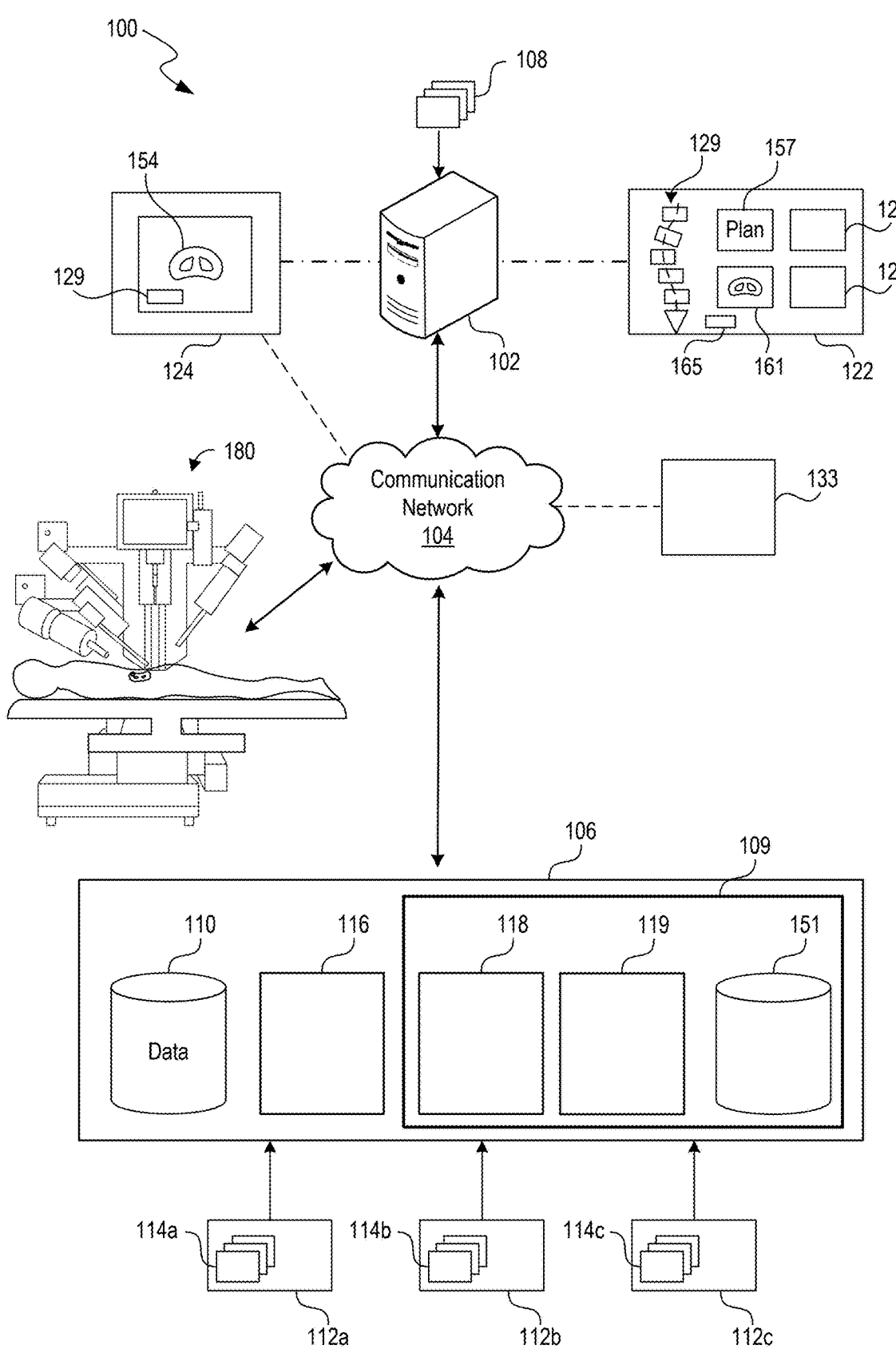
FIG. 1 is a network connection diagram illustrating a system for providing patient-specific medical care, according to an embodiment.

The present technology is directed to systems and methods for designing patient-specific treatments, implants, instruments, and/or systems. The present technology can include automated collection protocols for available third-party data to generate one or more plans (e.g., treatment plans, surgical plans, etc.), a set of plans, and/or patient-specific designs (e.g., orthopedic implant designs, instrument designs). The system can identify one or more triggers for collecting third-party data, search parameter(s) for selecting the data, etc. The triggers can be based on, for example, whether a database has insufficient data to design an implant with a quality score over a threshold, whether to generate or modify a machine learning module, identification of an edge case pathology in an internet search, results from performing a design check on an implant, identification of a new treatment, a type of implant or implant design, and/or detection of newly available data (e.g., data available in journal articles or publications, data approved by the U.S. Food and Drug Administration (FDA), etc.). The system can determine one or more scores (e.g., trust scores, confidence scores, etc.) for the collected third-party data based on, for example, the type of data, the source of the data, the similarity of the data to patient data, or combinations thereof. The system can select sets of third-party data and/or parameters in the third-party data used to design a patient-specific implant or patient treatment. Algorithms (e.g., machine learning algorithms or artificial intelligence (AI) algorithms) can be trained and retrained to identify third-party data similar to patient data and integrate the third-party data into patient treatment plans and/or patient-specific implant designs. In some embodiments, the collected third-party data can be displayed to a user (e.g., healthcare provider or patient) for modification and/or approval. In some embodiments, the method can compare the collected third-party data to patient data. This allows a user to visually identify differences and similarities between patient and third-party data.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

FIG. 1 is a network connection diagram illustrating a computing system 100 for providing patient-specific medical care, according to an embodiment. As described in further detail herein, the system 100 is configured to design patient-specific orthopedic implants and generate a medical treatment plan based on patient data, patient-specific implants, radiographic images, or the like. The system 100 includes a client computing device 102, which can be a user device, such as a smartphone, mobile device, laptop, desktop, personal computer, tablet, phablet, or other such devices known in the art. As discussed further herein, the client computing device 102 can include one or more processors, and memory storing instructions executable by the one or more processors to perform the methods described herein.

The client computing device 102 can be associated with a healthcare provider that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. In some embodiments, the patient data set 108 includes externally generated data, third-party data collected from external sources (e.g., remote servers, databases, websites, journals, articles, platforms, etc.), databases, software program platforms, navigation systems, treatment planning platforms, or combinations thereof. The databases can store, for example, machine learning (ML) modules, algorithms, models (e.g., anatomical models), etc. The client computing device 102 can communicate with one or more remote software program platforms. For example, the client computing device 102 can authenticate and receive data from authenticated software programs or platforms and use the received data to generate treatment plans. In some embodiments, the client computing device 102 can be periodically or continuously synchronized with the third-party data source. The third-party data source can include a computer-aided design (CAD) platform or application that updates models, and the updated models can be automatically sent to, or retrieved by, the client computing device 102. The client computing device 102 can validate the third-party model for treatment planning. For example, the third-party model can be validated by authenticating the third-party data source, translating the third-party model into a readable digital format, modifying the third-party virtual model for importation into an existing model, confirming that the imported third-party virtual model is compatible with other model elements, and/or importing all or a portion of the third-party virtual model and associated data (e.g., spinopelvic metrics or parameters). The imported third-party model can be, for example, a two-dimensional (2D), three-dimensional (3D) model, or other model of one or more anatomical elements, implants, navigation equipment, and/or instruments.

The client computing device 102 can communicate with the third-party data source such that the third-party data source modifies, replaces, or adjusts the data. In some embodiments, the client computing device 102 can be periodically or continuously synchronized with third-party treatment planning software, CAD software, navigation software, surgical robot software, user device (e.g., smartphone or tablet capturing images of surgery site), robotic surgery system, or the like. In some embodiments, the synchronization can be performed based on one or more synchronization triggers, including modification of data or event (e.g., publication of article(s), planned manufacturing of implant, start of surgery, etc.). In some embodiments, a user can set a schedule (e.g., daily, weekly, monthly, etc.) for synchronization using a mobile application.

The client computing device 102 can combine anatomical models from multiple third-party data sources to generate a multi-source anatomical model. The client computing device 102 can analyze, score, rank, and/or modify the multi-source anatomical mode to, for example, match patient images, predictions, surgical plans, etc. The anatomical models include standard models modifiable (e.g., scaled, sized, or altered to match patient data) based on patient data, patient-specific models with topology matching patient topology, etc. For example, the client computing device 102 can combine one or more standard models of anatomy, patient-specific models, models of implants, and other models to generate multi-source models. The multi-source models can be location models, topology models, and location-topology models. The location models can represent the anatomical positions of the patient anatomy. The topology models can represent the topology of the patient's anatomy. The location-topology models can represent both the position and the topology of the patient's anatomy. In some embodiments, the multi-source models can be 2D models, 3D models, etc. The client computing device 102 can include import and export modules, and the third-party data source can also include one or more design platforms The client computing device 102 and/or user can select metrics and/or parameters for the multi-source models.

The client computing device 102 can combine treatment plans from multiple third-party data sources to generate multi-source treatment plans. In some embodiments, the client computing device 102 can receive multiple treatment plans and integrate the plans together to generate a single multi-source treatment plan. The client computing device 102 can select a set of metrics from a first treatment plan and a second set of metrics from a second treatment plan. A multi-source treatment plan and a virtual anatomical model can be generated to achieve both the first and second sets of metrics. For example, the client computing device 102 can generate a multi-treatment plan based on the multiple individual treatment plans, such as an anterior fusion plan (e.g., a lumbar fusion plan for implanting one or more cages) and a posterior fusion plan (e.g., a fusion plan for implanting one or more rods). The multi-treatment plan can simulate outcomes associated with each treatment, spine pathology, and the like. The multi-treatment plan can be synchronized to update information (e.g., metrics, types of visual images, etc.) selected by, for example, a physician, healthcare provider, client computing device 102, machine learning module, or the like. The metrics and/or parameters can be from different models and/or treatment plans. In some embodiments, the multi-treatment plan can be updated based on modification(s) to a linked third-party source that provided a treatment plan.

In some embodiments, the client computing device 102 can be a third-party data source. The description of third-party data sources applies to the client computing device 102 unless indicated otherwise. For example, a user can select whether the computing device 102 generates plans and/or acts as a third-party data source supporting a remote system that generates plans. In some third-party data source embodiments, the computing device 102 can collect data, generate treatment data (e.g., models, predictions, corrected pathologies, navigation data, metrics, etc.) based on the collected data, and send the treatment data to a remote system that generates, based on the treatment data, one or more treatment plans, implant devices, etc. A user can review, revise, and/or approve treatment data and/or plans during this process.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from manufactures of surgical robots used in surgical procedures (e.g., robot positioning data, imaging data, navigation data, end effector data, etc.), data from imaging studies, data from simulations, clinical trials, demographic data, treatment data, outcome data, mortality rates, or the like. In some embodiments, the reference data includes third-party data collected from external sources (e.g., remote servers, databases, websites, journals, articles, social media networks, regulatory databases, insurance databases, etc.).

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112a-112c, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114a-114c, collectively 114) associated with reference patients treated by the corresponding healthcare provider. The reference patient data sets 114 can include, for example, electronic medical records, electronic health records, biomedical data sets, biomechanical data sets, mobility data sets, pain data sets, intra-operative image data, payment information, insurance information, insurer information, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices, etc.) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning and/or implant designing methods described herein. For example, in the depicted embodiment, the server 106 includes a data analysis module 116 and a third-party data collection platform 109 ("TPC platform 109").

The TPC platform 109 includes a third-party collection module 118, a data similarity module 119, and/or a database 151. In some embodiments, one or more of these modules may be combined with each other, or may be omitted. Thus, although certain operations are described herein with respect to a particular module or modules, this is not intended to be limiting, and such operations can be performed by a different module or modules in alternative embodiments. For example, the TPC platform 109 can be incorporated into the data analysis module 116. In some embodiments, the modules of the system 100 can be combined with modules of other systems. For example, the TPC platform 109 can be part of, or incorporated into, a healthcare system 133 and can manage the collection and analysis of third-party data for designing implants and generating healthcare plans. The TPC platform 109 can use machine learning to generate data confidence scores for the collected third-party data. The confidence scores can be generated based on a data type basis, and the confidence score can be ranked, weighted, and/or combined to determine an overall confidence score. For example, data-type confidence scores can indicate confidence level based on the type of data, including subjective data, objective data, or the like. A confidence score for high-confidence data, such as patient images (e.g., high-resolution X-rays or MRIs), peer-reviewed or authenticated journal articles, or other objective data, can be higher than a confidence score for low-confidence data, such as subjective data in the form of physician notes, non-peer-reviewed articles, pictures of a patient's posture, low-resolution X-rays, etc. U.S. Pat. No. 11,793,577 filed Oct. 24, 2023, and U.S. patent application Ser. No. 18/373,899 filed Sep. 27, 2023, disclose types of data, including image data, usable by the TPC platform 109 and are incorporated by reference in their entireties.

The TPC platform 109 can analyze collected data and group the collected data into subsets. The TPC platform 109 can then assign confidence scores to respective subsets of data. This allows for grouping and confidence-based ranking of grouped data. In some embodiments, the data analysis module 116 can group subsets of data, as discussed below. The database 151 can store collected third-party data, confidence scores, confidence scoring routines, and the like.

The data analysis module 116 is configured with one or more algorithms for identifying a subset of the third-party data from the database 151 that is likely to be useful in developing a patient-specific plan (e.g., treatment plan or another plan) and/or an implant design. For example, the data analysis module 116 can compare patient-specific data (e.g., the patient data set 108 received from the client computing device 102) to the third-party data from the database 151 (e.g., the third-party data sets) to identify similar data (e.g., one or more similar patient data sets in the third-party data sets). The comparison can be based on one or more metrics/parameters, such as age, gender, BMI, lumbar lordosis, pelvic incidence, and/or treatment levels. The metric(s)/parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each metric/parameter and determining the aggregate difference between the subject patient and each reference patient. Reference patients whose aggregate difference is below a threshold can be considered as similar patients.

The data analysis module 116 can further be configured with one or more algorithms to select a subset of the third-party patient data sets, e.g., based on similarity to the patient data set 108 and/or treatment outcome of the corresponding reference patient. For example, the data analysis module 116 can identify one or more similar patient data sets in the third-party data sets, and then select a subset of the similar patient data sets (e.g., a subset including portions of multiple data sets or a subset of entire data sets) based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value. A user can set the threshold value, or the data analysis module 116 can calculate the threshold value. If the outcome score meets retraining criteria (e.g., outcome score not meeting an accuracy score), machine learning module(s) can be retrained using the patient data. The retraining criteria can be inputted by a user, calculated based on accuracy of the confidence scoring algorithms, or the like.

In some embodiments, the data analysis module 116 selects a subset of the third-party data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively. In some embodiments, the data analysis module 116 can identify similarities and/or differences between the third-party data and the patient data. For example, similar spine metrics can be highlighted and correlated in tables. A user can visually identify the number and types of correlated data to determine whether sufficient similarities exist between the third-party data and the patient data. In some embodiments, the user can input information for determining similarities and/or outcome parameters.

In some embodiments, the data analysis module 116 includes one or more algorithms used to select a set or subset of the third-party data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient-related information that can be used to predict outcomes and risk profiles for procedures for the present healthcare provider. For example, third-party data sets with images captured from similar diagnostic equipment can be aggregated to reduce or limit irregularities due to variation between diagnostic equipment. Additionally, patient-specific treatment plans can be developed for a particular healthcare provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data sets, and other data sets can be utilized. By way of example, a patient-specific treatment plan to perform a battlefield surgery can be based on reference patient data from similar battlefield surgeries and/or data sets associated with battlefield surgeries. In another example, the patient-specific treatment plan can be generated based on available robotic surgical systems. The third-party data sets can be selected based on patients that have been operated on using comparable robotic surgical systems under similar conditions (e.g., size and capabilities of surgical teams, hospital resources, etc.).

The TPC platform 109 can include the third-party collection module 118, the data similarity module 119, and the database 151. The TPC platform 109 can be a design platform linked to one or more clinical data sources for third-party data (crowdsourcing) integration based on clinical literature confidence. The TPC platform 109 can establish one or more links with surgical robots, remote server platforms supporting surgical robots, navigation systems, and/or other equipment. The system 100 can authenticate the equipment, received software, received data, remote server platforms, or the like. In some embodiments, the TPC platform 109 can perform one or more processes (e.g., authentication processes, encryption/decryption processes, data integration processes, etc.) so that the link can be an encrypted link to communicate, for example, encrypt search requests, third-party data, or the like. Example encrypted third-party data can include one or more training items (e.g., training items for ML modules, AI modules, etc.), ML algorithms, generative AI data, ML/AI databases, virtual model data, CAD data, prior patient data, non-anonymized historical data (e.g., prior patient data, physician notes, etc.), biometric data, request-specific packets of data, trade secret information, or the like. In some embodiments, the link is a non-encrypted link.

In some embodiments, the data similarity module 119 is configured to develop and/or implement at least one predictive model for identifying third-party data similar to patient data. The TPC platform 109 can include a design platform linked to one or more databases and/or model sources for third-party data model integration based on, for example, model confidence. The TPC platform 109 can determine model confidences based on the third-party data source, comparisons of the models to patient data, etc. For example, a patient-specific topology/position model can be assigned a model confidence score higher than patient-specific location models (e.g., a virtual model without topology information).

Predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan or implant design will produce a favorable outcome for the particular patient. The predictive model(s) can be validated, e.g., by inputting data into the model(s) and comparing the output of the model to the expected output. Additionally or alternatively, the TPC platform 109 can develop one or more anatomical outcomes (e.g., predicted post-operative anatomical outcome), plans (e.g., patient-specific surgical plans, treatment plans, etc.), implant designs, or the like. Machine learning models can be trained to analyze third-party data to identify any similarities to patient data.

Alternatively or in combination, the third-party collection module 118 can collect and analyze third-party data using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the third-party collection module 118 collects and analyzes third-party data using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in the database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training data set can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set can fluctuate during training, such that ad hoc rules may be used to decide when overfitting has truly begun. Finally, a test data set can be used to provide an unbiased evaluation of a final model fit on the training data set.

To generate one or more treatment plans and/or implant designs, the third-party data can be input into the trained machine learning model(s). Additional data, such as the selected subset of the third-party data sets and/or similar patient data sets (e.g., electronic medical records, patient images, etc.), and/or treatment data from the selected subset, can also be input into the trained machine learning model(s). The trained machine learning model(s) can then calculate whether various candidate treatment procedures and/or medical device designs (e.g., patient-specific orthopedic implants) are likely to produce a favorable outcome for the patient, or meet one or more parameters (e.g., coverage parameters, reimbursement parameters, regulatory parameters, or the like). Based on these calculations, the trained machine learning model(s) can select data, data sources, etc. used to generate treatment plans. Additionally or alternatively, based on these calculations, the trained machine learning model(s) can select at least one treatment plan or implant design for the patient. In embodiments where multiple trained machine learning models are used, the models can be run sequentially or concurrently to compare outcomes and can be periodically updated using training data sets. The third-party collection module 118 can use one or more of the machine learning models based the model's predicted accuracy score.

The third-party data collected and analyzed by the third-party collection module 118 can be transmitted via the communication network 104 to the client computing device 102 for output to a user (e.g., clinician, surgeon, healthcare provider, patient). In some embodiments, the client computing device 102 includes, or is operably coupled to, a display 122 for showing the third-party data. The client computing device 102 can notify a user that third-party data is available, found, collected, and/or analyzed. In some embodiments, the client computing device 102 or system can send one or more requests for data based on a determination of deficient data and/or decrypt received encrypted third-party data. The determination of deficient data can be based on insufficient available data for predicting an acceptable outcome, predicting an outcome with threshold likelihood of outcome score, generating a complete virtual model (e.g., an incomplete model of devices or implants), etc. In some embodiments, requests can be sent in response to pre-operatively and/or intra-operatively determined based on an insufficient amount of navigation data, insufficient data for controlling a surgical robot, insufficient data for simulations (e.g., simulations with a digital twin of the patient, simulations of robotic surgical procedures, etc.), etc. In some embodiments, the ML and/or AI modules can determine one or more requests for third-party data based on pre-operative training performed by the surgical team. The third-party data can be incorporated into the training to improve training and patient outcomes. The third-party data can be successful prior procedures, alternative treatment plans, or the like.

The client computing device 102 or system can receive third-party data for the surgical robot 180. The third-party data can include, for example, control software for the surgical robot 180, navigation software, data (e.g., navigation data, historical procedure data, training data for training using the surgical robot 180, etc.), virtual models of the surgical robot 180, virtual models of end effectors, or combinations thereof. The client computing device 102 can integrate control GUIs into surgical plans so that the control GUIs can be used to control the surgical robot 180 while performing the robotic procedure. The control GUI can include control inputs (sliders, menus, etc.) for controlling end effectors, robotic instruments, robotic arms, imaging equipment, etc., and the GUI can be inserted into, overlay, or be incorporated into treatment GUIs. The system 100 can synchronize treatment plans and operation of the surgical robot such that modifier events automatically modify surgical plans, control of the surgical robot, etc. The modifier events can include, for example, changes and/or deviations to surgical procedures, surgical plans, etc. and include modifying locally stored surgical plans, remotely stored surgical plans (e.g., surgical plans stored on remote third-party servers), etc.

The surgical robot 180 may adapt dynamically to changing surgical procedures and/or plans through real-time updates and adjustments. As modifications are made to the surgical procedure or plan, either manually by the surgeon or automatically based on intraoperative data, the system 100 can transmit these changes to the surgical robot 180. The robot's control software may then recalibrate its movements, adjust instrument trajectories, or modify end effector positions to align with the updated plan. In some cases, the surgical robot 180 may utilize machine learning algorithms to anticipate and safely transition between different surgical steps as the plan evolves. The robot may also integrate feedback (e.g., data from its sensors and imaging systems, navigation system feedback, etc.) to refine its actions in response to the changing surgical environment. This adaptive capability can allow the surgical robot 180 to maintain precision and safety while accommodating unexpected variations or optimizations in the surgical approach.

The client computing device 102 can periodically query data sources (e.g., remote servers, databases, websites, etc.) to determine whether new data is available. The newly available data can be analyzed to determine whether it may be clinically relevant to planned treatments. If so, the client computing device 102 can collect and analyze the newly available data to determine whether the planned treatment should be modified based on the new data. In response to determining that a user should review the data or the planned treatment should be modified, the client computing device 102 can send a notification to the user based on the newly available data. In some embodiments, the notification can indicate that newly available data could be used to modify a planned treatment. In some embodiments, the notification can include a modified treatment plan based on the newly available data. A user can compare the previous planned treatment to the modified planned treatment to determine which planned treatment to pursue. For example, a user device or display 122 can concurrently display the previous planned treatment, the modified planned treatment, and differences between the two. This process can be used to modify treatment plans, implant designs, or the like.

The display 122 can include a graphical user interface (GUI) for visually depicting various aspects of third-party data, including similarities or differences in comparison to data of the patient. The client computing device 102 can further include one or more user input devices (not shown) allowing the user to modify, select, approve, and/or reject the displayed treatment plan(s), data sources, sets of data, etc. The display 122 can display the source of the third-party data, selectors (e.g., selector boxes, menus, etc.) for selecting or deselecting the sources (e.g., selecting for detailed review of third-party data), or the like. The display 122 can then display third-party data only from user-selected sources. This allows a user to navigate available data sources that are trusted by the user. Selected third-party sources can be linked to the system for continuous or periodic queries. If the third-party data source is updated, the system can automatically search the third-party data source to determine whether newly available data should be used. A notification can be sent to the user if the third-party data source becomes unavailable.

In some embodiments, the user can select or deselect sets of data. If the user deselects a set of third-party data (e.g., a set of data based on a particular population group), a treatment plan can be updated without using the deselected third-party data. In some embodiments, the display 122 can show different treatments based on whether third-party data sets or sources are used. In some embodiments, the user can select or deselect types of data (e.g., images, text, reference patient data, data from studies, etc.) to be collected. In some embodiments, the user or system can select sets of metrics/parameters from treatment plans to generate a new treatment plan for achieving the selected metrics/parameters.

The display 122 can also include controls for receiving data from remote or third-party applications or programs. For example, a user can select one or more treatment planning applications on remote servers, and those selected applications can generate treatment plans, which can be consolidated into a single plan. In some embodiments, the display 122 can display a first plan for intervertebral cages manufactured by a first company. The display 122 can concurrently or sequentially display a second plan for instruments or surgical equipment from a second company. The display 122 can show a single surgical procedure plan with post-operative outcomes associated with the first and/or second plans.

The system can acquire third-party robotic data for similar procedures and/or patients to, for example, generate the surgical plans, control operation of the surgical robot, simulate surgical steps to be performed, simulate patient outcomes, or the like. In some embodiments, the display 122 displays a first robotic surgical plan for a surgical procedure performed by a first surgical robot. The display 122 can concurrently or sequentially display (1) the first robotic surgical plan and (2) a second robotic surgical plan for a surgical procedure performed by a second surgical robot different from the first surgical robot. The display 122 can show the same general surgical procedure plan with post-operative outcomes associated with the first and/or second surgical robots. A user can select whether the first or second robot, or both, will be perform the surgical procedure. The display 122 can also concurrently display manual surgical plan(s), robotic-assisted surgical plan(s), and/or robotic surgical plan(s).

To facilitate visualization, the display 122 can display one or more patient images, virtual models, and associated metrics/parameters, including pre-operative metrics/parameters, planned metrics/parameters, and/or post-operative metrics/parameters. As another example, the display 122 can show a design for a medical device to be implanted in the patient, such as a 2D or 3D model of the device design. The device design can include, for example, a size and configuration of an implant (e.g., footprint of intervertebral cage), length and curvature of spinal rods, length and characteristics of screws (e.g., bone screws, pedicle screws), range of motion of artificial discs, or the like. The display 122 can also show patient information, such as 2D or 3D images or models of the patient's anatomy where the surgical procedure is to be performed and/or where the device is to be implanted. In some procedures, the system can design implants based on received third-party data related to the size of the implant. For example, the size of the implant (e.g., an interbody cage or an artificial disc) can be a percentage of vertebral endplate(s), percentage of original disc height prior to surgery, or the like. In some procedures, the system can design implants based on received third-party data related to the curvature of the patient's spine. For example, a length, curvature, and strength of the implants (e.g., spinal rods) can be designed based on the received third-party curvature data.

The display 122 can display recommended types of implants, procedures (e.g., levels of treatment in spine procedures), placement criteria, contact interface criteria, loading criteria, properties of implants, characteristics of implants, or the like. In spine procedures, the type of implant can be, for example, a fixed intervertebral cage, an artificial disc, a rod, etc. selected based on whether the system determines there should be mobility at spinal levels. The placement criteria can include, for example, distance from anatomical features, position with respect to the perimeter of a vertebral endplate or body, and/or other positional location. In some spinal fusion procedures, the coverage criteria can include, for example, maximum or minimum percentage of coverage of the vertebral endplate, areas of coverage along the vertebral endplate, or the like. The load-bearing characteristics can include, for example, strength of the implant, fracture toughness of the implant, fatigue life of implant, degrees of motion of the implant, or the like. The characteristics of the implant can include, for example, lattice characteristics (e.g., density of lattice structure, distribution of lattice structure), openings for receiving grafting material, or the like. The display 122 can display recommendations for other procedures.

The TPC platform 109 can perform one or more simulations using 3D models, labeled patient images, modified patient images, or the like. The TPC platform 109 can measure the patient's anatomy based on the 3D models or modified patient images (e.g., patient images with anatomical features repositioned). In some embodiments, the TPC platform 109 can build virtual implants using the third-party data or a combination of the third-party data and the patient's data. The virtual implants and 3D models of the patient can be used to generate one or more simulations. The simulations can be dynamic/biomechanic simulations of the patient with real-time data (e.g., weight, BMI, etc.) collected from a user device (e.g., wearable device, Internet of Things (IoT) device, etc.) to predict the success of installing an implant in the patient. The TPC platform 109 can evaluate the dynamic/biometric simulations to determine, for example, whether additional third-party data should be collected, whether additional relevant third-party data is available, etc. In response to determining that additional data should be collected or is available, the TPC platform 109 can search for data, determine whether to terminate the search (e.g., to limit usage of processing resources), determine whether to generate target searches to manage resources, and/or delete all or some of the collected data to manage memory usage. The TPC platform 109 can collect data (e.g., periodically or continuously collect data) for one or more time periods, a pre-manufacturing period, a pre-operative time period, a post-operative time period, etc. In some embodiments, the TPC platform 109 can retrieve virtual implants, simulations performed on a digital twin of the patient, simulated patient outcomes, and/or other information disclosed herein from third-party servers or databases.

The TPC platform 109 can determine whether to use available information. The determination can be based on one or more of a confidence score for the available data (e.g., a confidence score exceeding a threshold score), user setting value (e.g., a user-inputted search alert query), etc. The system can notify the user of the newly available data. In response to the system determining that the newly available third-party data should be used, the user can be notified prior to generating a newly modified treatment plan based on the newly available data. The system can modify treatments in real-time or near real-time so that the user can determine in real-time or near real-time whether to pursue the planned treatment or a newly modified treatment. In another example, the user can be notified that newly available third-party data could be used to modify designs of one or more implants or instruments.

In some embodiments, the medical device design(s) generated by the server 106 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. Manufacturing can be achieved using human design, machine design, a combination of human and machine design, or other design techniques. For example, the manufacturing system 124 can be configured for additive manufacturing, such as 3D printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. The manufacturing system 124 can be controlled to generate components with target characteristics (e.g., mechanical characteristics, lattice structure characteristics, porosity, surface finishes, etc.). Example components and implants are discussed in connection with FIGS. 12A-13. Alternatively or in combination, the manufacturing system 124 of FIG. 1 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The manufacturing system 124 and the implant analyzer 129 can communicate directly with one another or via the communication network 104. The system 100 can perform one or more validation steps for a manufactured implant. The analyzer 129 can include one or more scanners, cameras, or imaging devices and can be incorporated into the manufacturing system 124 or other components of the system 100 and can scan the manufactured implant to, for example, identify manufacturing defects, confirm the implant meets one or regulatory requirements, etc. By analyzing implant characteristics (e.g., composition of the material, surface topology, etc.) and manufacturing parameters (e.g., composition of the material, temperature, speed of printing, manufacturing conditions, accuracy of printer, etc.), the system 100 can determine whether the implant should be implanted in a patient. If the implant is not acceptable, system 100 can determine manufacturing adjustments for the implant to be remanufactured. The analyzer 129 can be onsite manufacturing scanners positioned to scan implants during and/or after fabrication. In some embodiments, the analyzers 129 are offsite of the manufacturing location. For example, the analyzers 129 can be located at a healthcare provider (e.g., at a hospital, clinic, surgical suite, etc.) to allow quality control checking immediately prior to implantation, verification of regulatory compliance, etc.

The manufacturing system 124 can manufacture all or some of the components of a kit. The kit components can be selected based on requirement(s), including regulatory requirements, reimbursement requirements, or other requirements. Surgical kits can include one or more implants, instruments, instructions for use, and reusable and disposable components. The kit requirements can be retrieved from a database 151. The system 100 can synchronize the surgical plan with the requirements to generate patient-specific surgical kits meeting the requirements.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. The control instructions can be transmitted to the robotic apparatus by the client computing device 102 and/or the server 106.

Following the treatment of the patient in accordance with the treatment plan, treatment progress can be monitored over one or more time periods to update the data analysis module 116. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116, and/or the third-party collection module 118 can be components of the client computing device 102, rather than the server 106. As another example, the database 110, the data analysis module 116, and/or the third-party collection module 118 can be located across a plurality of different servers, computing systems, or other types of cloud-computing resources, rather than at a single server 106 or client computing device 102.

The display 122 can display an intra-operative data 123 and pre-operative data 127 virtually overlaid on each other to illustrate the placement and position of the implant 161. A user can review proposed pathology 129, a treatment plan 157, and implant(s) 161. The treatment plan 157 can be an interactive plan having a user input element 165 (e.g., one or more buttons, a dropdown menu, toggle, etc.) for modification and/or approval. The intra-operative data 123 and pre-operative data 127 can be dynamically updated based on the user input. This allows a user to identify the intra-op positioning of surgical implants based on the pre-operative plan. The display 122 can graphically overlay an intra-operative image over a pre-operative plan/model/image. A user (e.g., healthcare provider, such as a surgeon) can manipulate (e.g., zoom, stretch, crop, and/or rotate) the intra-operative image to align with the pre-operative model (e.g., virtual 3D model), images (e.g., images of virtual models), anatomical renderings, or other images displaying anatomical position information on the device. In some cases, a user can zoom, stretch, and/or rotate the virtual 3D model (or other pre-operative images) to align with the intra-operative image on the device or other viewing platform.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
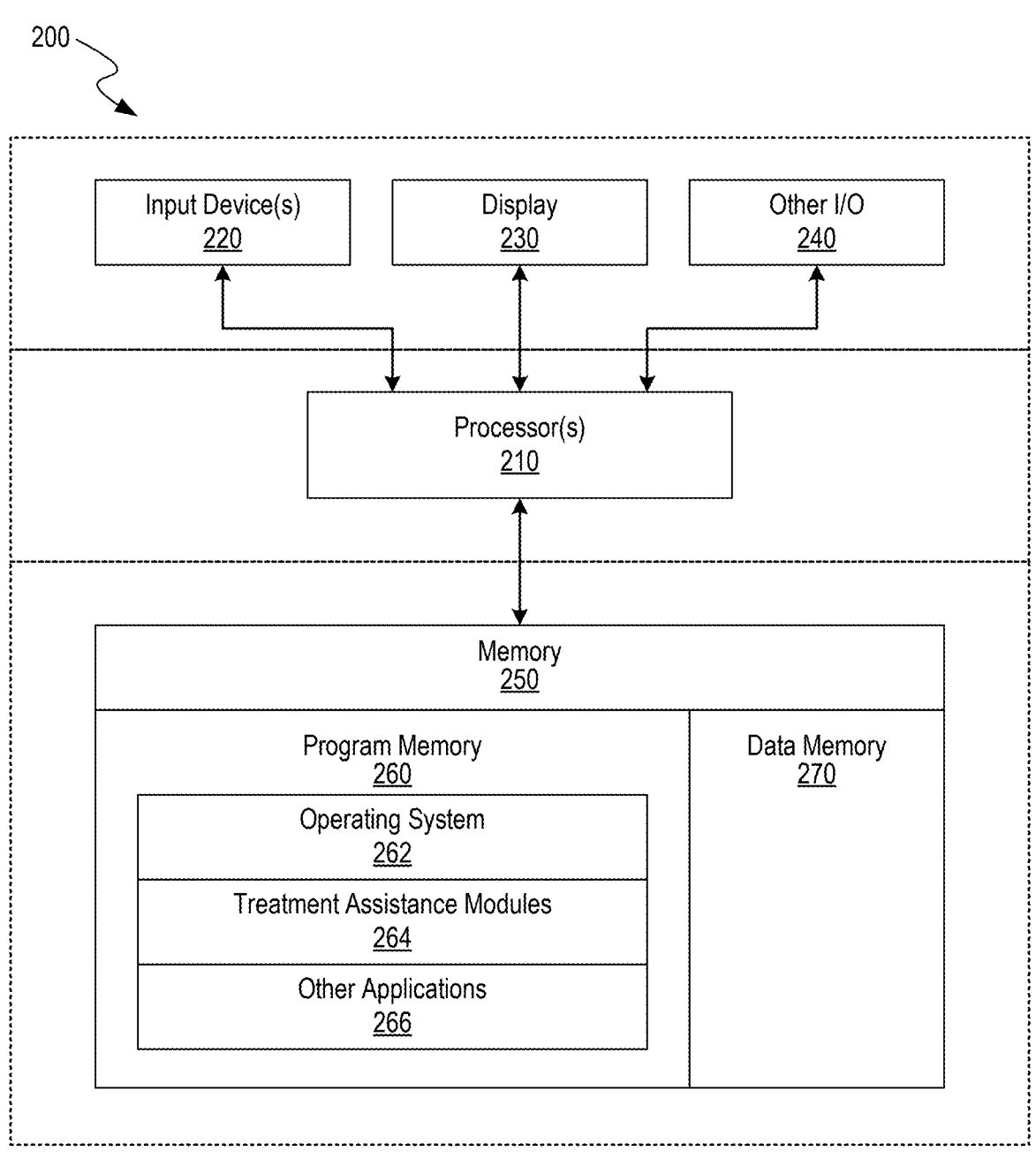
FIG. 2 illustrates a computing device suitable for use in connection with the system of FIG. 1, according to an embodiment.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or the third-party collection module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
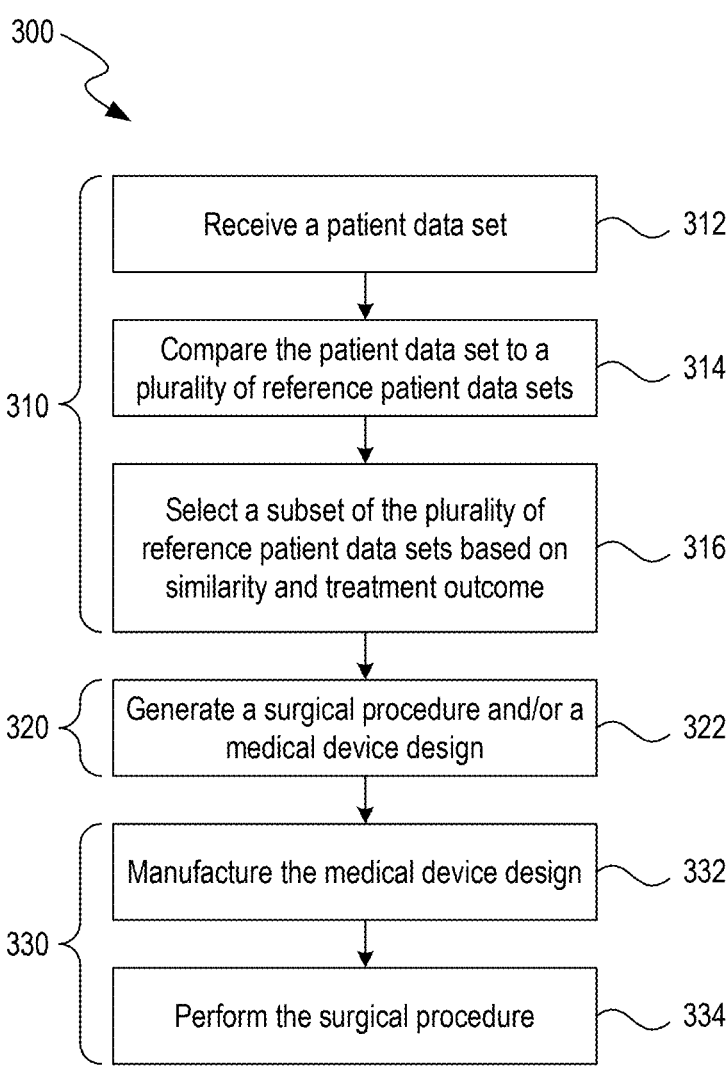
FIG. 3 is a flow diagram illustrating a method for providing patient-specific medical care, according to an embodiment.

FIG. 3 is a flow diagram illustrating a method 300 for providing patient-specific medical care, according to an embodiment. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, coronal offset distance, segment flexibility, LL-PI is greater than predetermined degrees (e.g., 5 degrees, 10 degrees, etc.), LL-PI mismatch (e.g., age-adjusted), sagittal vertical axis offset distance, coronal offset distance, coronal angle, bone quality, rotational displacement, or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually, by a surgical robot, or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

Figure 4A:
FIGS. 4A-4C illustrate exemplary data sets that may be used and/or generated in connection with the methods described herein, according to an embodiment.
Figure 4B:
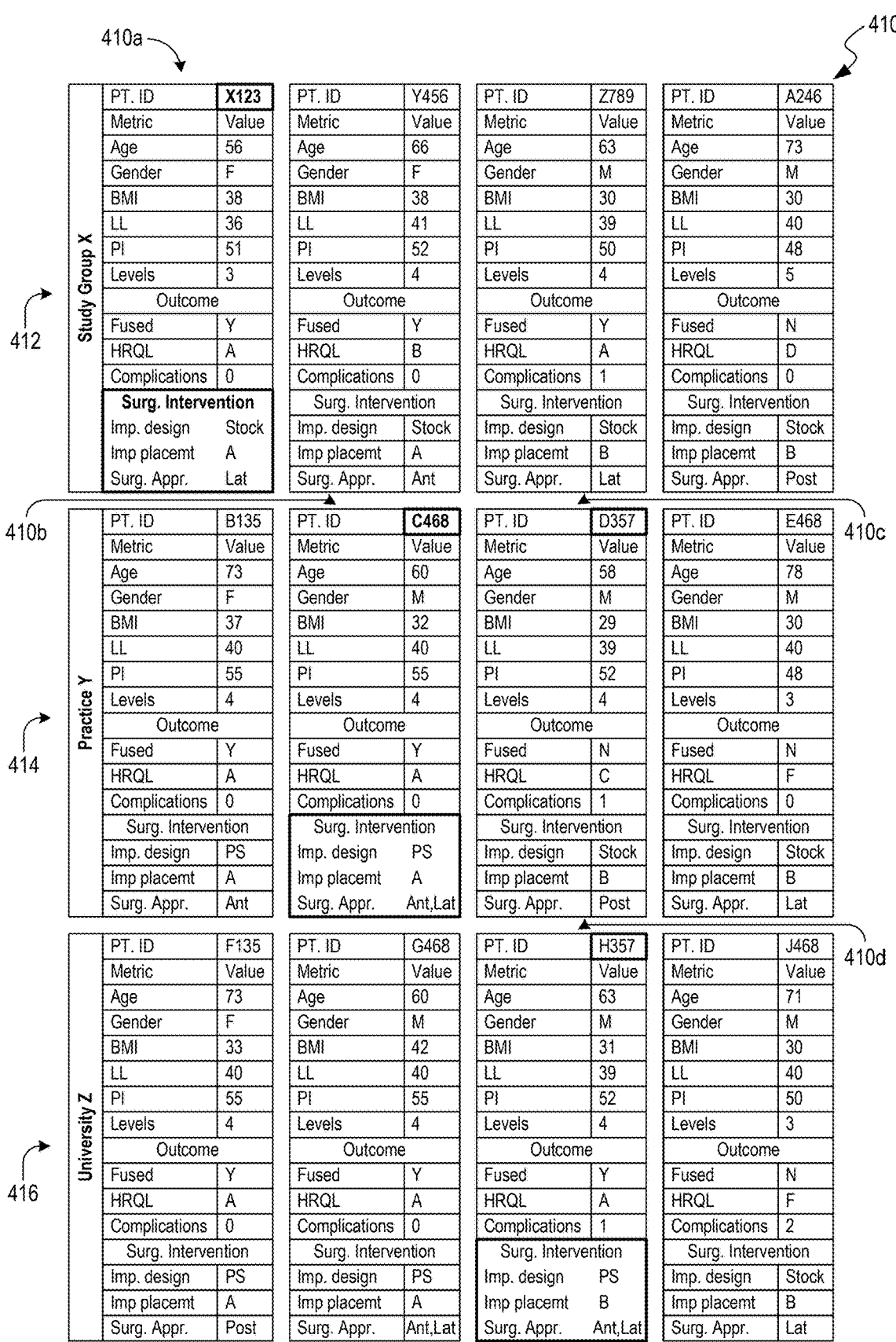
Figure 4C:
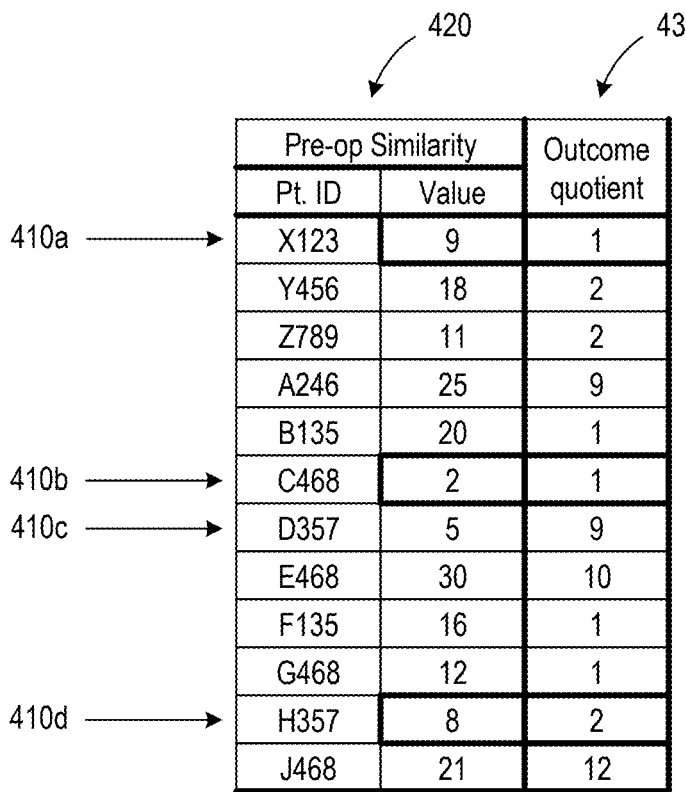

FIGS. 4A-4C illustrate exemplary data sets that may be used and/or generated in connection with the methods described herein (e.g., the data analysis phase 310 described with respect to FIG. 3), according to an embodiment. FIG. 4A illustrates a patient data set 400 of a patient to be treated. The patient data set 400 can include a patient ID and a plurality of pre-operative patient metrics (e.g., age, gender, BMI, lumbar lordosis (LL), pelvic incidence (PI), and treatment levels of the spine (levels)). FIG. 4B illustrates a plurality of reference patient data sets 410. In the depicted embodiment, the reference patient data sets 410 include a first subset 412 from a study group (Study Group X), a second subset 414 from a practice database (Practice Y), and a third subset 416 from an academic group (University Z). In alternative embodiments, the reference patient data sets 410 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 4C illustrates comparison of the patient data set 400 to the reference patient data sets 410. As previously described, the patient data set 400 can be compared to the reference patient data sets 410 to identify one or more similar patient data sets from the reference patient data sets. In some embodiments, the patient metrics from the reference patient data sets 410 are converted to numeric values and compared the patient metrics from the patient data set 400 to calculate a similarity score 420 ("Pre-op Similarity") for each reference patient data set. Reference patient data sets having a similarity score below a threshold value can be considered to be similar to the patient data set 400. For example, in the depicted embodiment, reference patient data set 410a has a similarity score of 9, reference patient data set 410b has a similarity score of 2, reference patient data set 410c has a similarity score of 5, and reference patient data set 410*d* has a similarity score of 8. Because each of these scores are below the threshold value of 10, reference patient data sets 410*a-d* are identified as being similar patient data sets.

The treatment outcome data of the similar patient data sets 410*a-d* can be analyzed to determine surgical procedures and/or implant designs with the highest probabilities of success. For example, the treatment outcome data for each reference patient data set can be converted to a numerical outcome score 430 ("Outcome Quotient") representing the likelihood of a favorable outcome. In the depicted embodiment, reference patient data set 410*a* has an outcome score of 1, reference patient data set 410*b* has an outcome score of 1, reference patient data set 410*c* has an outcome score of 9, and reference patient data set 410*d* has an outcome score of 2. In embodiments where a lower outcome score correlates to a higher likelihood of a favorable outcome, reference patient data sets 410*a*, 410*b*, and 410*d* can be selected. The treatment procedure data from the selected reference patient data sets 410*a*, 410*b*, and 410*d* can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof.

In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

Figure 5:
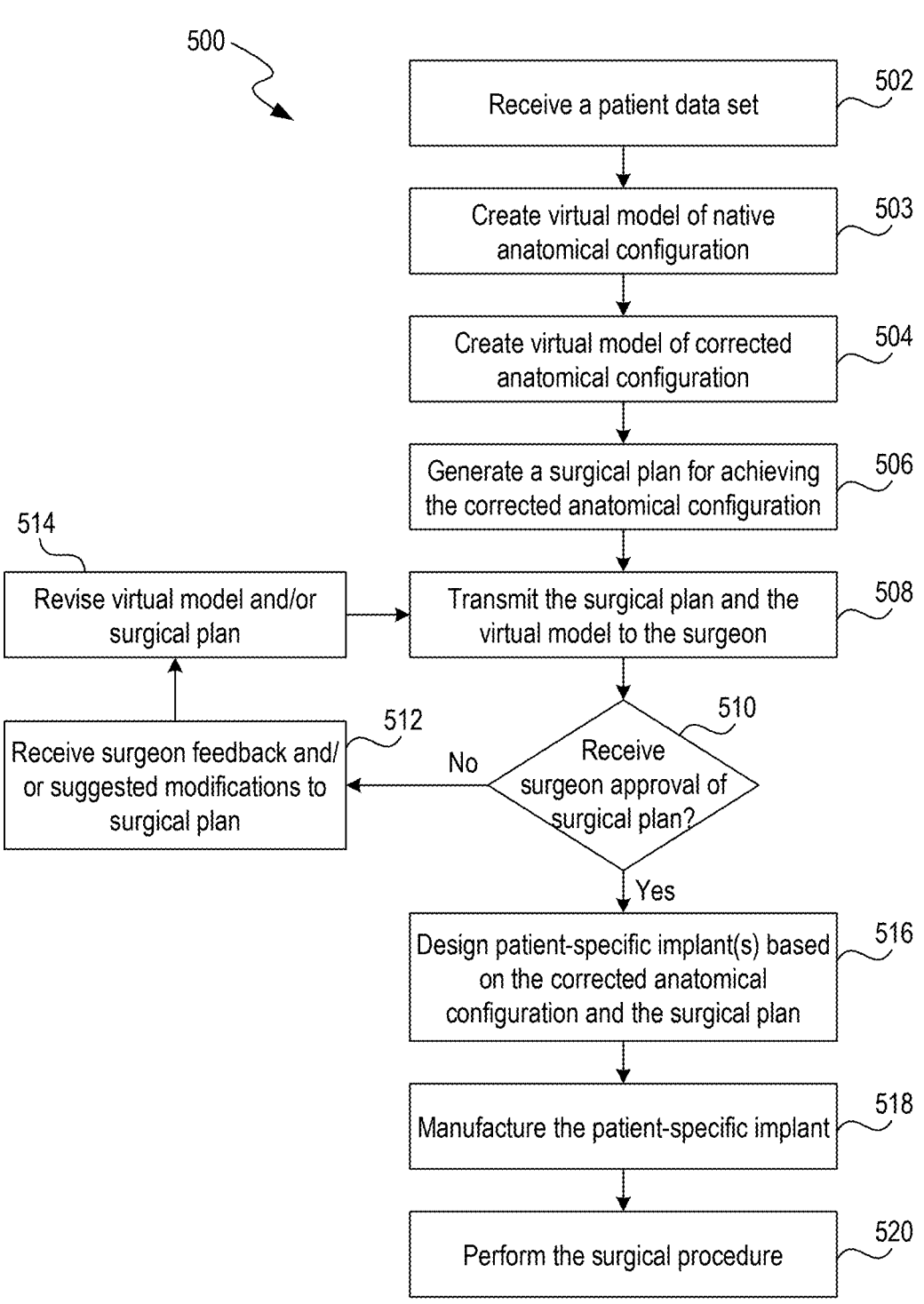
FIG. 5 is a flow diagram illustrating another method for providing patient-specific medical care, according to an embodiment.

FIG. 5 is a flow diagram illustrating a method 500 for providing patient-specific medical care, according to another embodiment of the present technology. The method 500 can begin in step 502 by receiving a patient data set for a particular patient in need of medical treatment. The patient data set can include data representative of the patient's condition, anatomy, pathology, symptoms, medical history, preferences, intra-operative data, and/or any other information or parameters relevant to the patient. For example, the patient data set 850 can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-ray images, and the like. In some embodiments, the patient data set includes data representing one or more of patient ID, age, gender, BMI, lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1. In some embodiments, the computing system that receives the patient data set in step 502 also stores one or more software modules (e.g., the data analysis module 116 and/or the third-party collection module 118, shown in FIG. 1, or additional software modules for performing various operations of the method 500). Additional details for collecting and receiving the patient data set are described below with respect to FIGS. 6-7D. In some embodiments, the patient data set includes selected third-party data, as described in FIGS. 6A-6C.

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a 2D or 3D visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 8A and 8B. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected anatomical configuration (which can also be referred to herein as the "planned configuration," "optimized geometry," "post-operative anatomical configuration," or "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4C (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, etc.). Target post-operative metrics can include, but are not limited to, target coronal parameters, target sagittal parameters, target pelvic incidence angle, pelvic tilt, thoracic kyphosis, sacral slope, target Cobb angle, target shoulder tilt, target iliolumbar angle, target coronal balance, target Cobb angle, target lordosis angle, spinopelvic parameters, and/or a target intervertebral space height. The different between the native anatomical configuration and the corrected anatomical configuration may be referred to as a "patient-specific correction" or "target correction." In some embodiments, the virtual model of the corrected anatomical configuration of the patient can also be based, at least in part, on the third-party data selected in FIGS. 6A-6C.

Once the corrected anatomical configuration is determined, the computing system can generate a 2D or 3D visual representation of the patient's anatomy with the corrected anatomical configuration. As with the virtual model created in step 503, the virtual model of the patient's corrected anatomical configuration can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region in a corrected anatomical configuration, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 9A-1-9B-2.

In step 504, images of the patient can be segmented to isolate separate anatomic elements of the anatomy of interest. The spatial relationships between the isolated anatomic elements can be modified to generate a target or corrected patient pathology. The modifications can be selected based on regulatory criteria, financial parameters, etc. Other techniques can be used to generate anatomical configurations based on the available patient data.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, etc.) across a specific range of vertebral levels (e.g., L1-L4, L1-5, L3-T12, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, coronal parameters, sagittal parameters, and/or pelvic parameters) corresponding to the expected post-operative patient anatomy. The surgical plan can be generated by the same or different computing system that created the virtual model of the corrected anatomical configuration. In some embodiments, the surgical plan can also be based on one or more reference patient data sets as previously described with respect to FIGS. 1-4C. In some embodiments, the surgical plan can also be based at least in part on surgeon-specific preferences and/or outcomes associated with a specific surgeon performing the surgery. In some embodiments, more than one surgical plan is generated in step 506 to provide a surgeon with multiple options. An example of a surgical plan is described below with respect to FIGS. 10A and 10B. In some embodiments, the surgical plan can also be based at least in part on the third-party data selected in FIGS. 6A-6C.

After the virtual model of the corrected anatomical configuration is created in step 504 and the surgical plan is generated in step 506, the method 500 can continue in step

508 by transmitting the virtual model of the corrected anatomical configuration and the surgical plan, including interactive surgical plans, for surgeon review. In some embodiments, the virtual model and the surgical plan are transmitted as a surgical plan report, an example of which is described with respect to FIG. 11. In some embodiments, the same computing system used in steps 502-506 can transmit the virtual model and surgical plan to a computing device for surgeon review (e.g., the client computing device 102 described in FIG. 1). This can include directly transmitting the virtual model and the surgical plan to the computing device or uploading the virtual model and the surgical plan to a cloud or other storage system for subsequent downloading. Although step 508 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 508 may include the virtual model of the patient's native anatomical configuration (or images thereof) in addition to the virtual model of the corrected anatomical configuration. In embodiments in which more than one surgical plan is generated in step 506, the method 500 can include transmitting more than one surgical plan to the surgeon for review and selection.

The surgeon can perform an implant design check by reviewing the virtual model and surgical plan and, in step 510, either approve or reject the surgical plan (or, if more than one surgical plan is provided in step 508, select one of the provided surgical plans). If the surgeon does not approve the surgical plan in step 510, the surgeon can optionally provide feedback and/or suggested modifications to the surgical plan (e.g., by adjusting the virtual model or changing one or more aspects about the plan). Accordingly, the method 500 can include receiving (e.g., via the computing system) the surgeon feedback and/or suggested modifications. If surgeon feedback and/or suggested modifications are received in step 512, the method 500 can continue in step 514 by revising (e.g., automatically revising via the computing system) the virtual model and/or surgical plan based at least in part on the surgeon feedback and/or suggested modifications received in step 512. In some embodiments, the surgeon does not provide feedback and/or suggested modifications if they reject the surgical plan. In such embodiments, step 512 can be omitted, and the method 500 can continue in step 514 by revising (e.g., automatically revising via the computing system) the virtual model and/or the surgical plan by selecting new and/or additional reference patient data sets. The revised virtual model and/or surgical plan can then be transmitted to the surgeon for review. Steps 508, 510, 512, and 514 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 510, the method 500 can continue in step 516 by designing (e.g., via the same computing system that performed steps 502-514) a patient-specific implant based on the corrected anatomical configuration and the surgical plan. The implant(s) (e.g., implants 154 or 161 of FIG. 1) can be designed by mapping a negative space between the anatomic elements and filling at least a portion of the negative space with a medical virtual implant. U.S. application Ser. No. 16/569,494 discloses techniques for generating corrected patient pathologies, mapping spaces, designing implants, and manufacturing implants. U.S. application Ser. No. 16/569,494 is incorporated by reference in its entirety.

The patient-specific implant can be specifically designed such that, when it is implanted in the particular patient, it directs the patient's anatomy to occupy the corrected anatomical configuration (e.g., transforming the patient's anatomy from the native anatomical configuration to the corrected anatomical configuration). The patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific implant is designed solely based on the virtual model of the corrected anatomical configuration and/or without reference to pre-operative patient images. In some embodiments, the patient-specific implant is designed based at least in part on the third-party data selected in FIGS. 6A-6C.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors (e.g., bone screws), nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.). An example of a patient-specific implant designed via the method 500 is described below with respect to FIGS. 12A and 12B.

In some embodiments, designing the implant in step 516 can optionally include generating fabrication instructions for manufacturing the implant. For example, the computing system may generate computer-executable fabrication instructions that that, when executed by a manufacturing system, cause the manufacturing system to manufacture the implant. For example, a virtual 3D model of the one or more patient-specific implants can be created based on filling of negative spaces between anatomical elements of the corrected patient pathology. The virtual 3D model can be converted into 3D fabrication data for manufacturing the one or more patient-specific implants.

In some embodiments, the patient-specific implant is designed in step 516 only after the surgeon has reviewed and approved the virtual model with the corrected anatomical configuration and the surgical plan. Accordingly, in some embodiments, the implant design is neither transmitted to the surgeon with the surgical plan in step 508, nor manufactured before receiving surgeon approval of the surgical plan. Without being bound by theory, waiting to design the patient-specific implant until after the surgeon approves the surgical plan may increase the efficiency of the method 500 and/or reduce the resources necessary to perform the method 500.

The method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1). In some embodiments, the implant is manufactured by the manufacturing system executing the computer-readable fabrication instructions generated by the computing system in step 516.

Once the implant is manufactured in step 518, the method 500 can continue in step 520 by implanting the patient-specific implant into the patient. The surgical procedure can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure.

The method 500 can be implemented and performed in various ways. In some embodiments, steps 502-516 can be performed by a computing system associated with a first entity, step 518 can be performed by a manufacturing system associated with a second entity, and step 520 can be performed by a surgical provider, surgeon, and/or robotic surgical platform associated with a third entity. During the surgical procedure, method 500 can collect intra-operative data. Any of the foregoing steps may also be implemented as computer-readable instructions stored in memory and executable by one or more processors of the associated computing system(s). In some implementations, steps 502-514 are performed with intra-operative data to provide confirmation that the location and position of the implant during a surgical procedure is within a threshold (e.g., delta threshold) of the pre-operative plan.

Figure 6A:
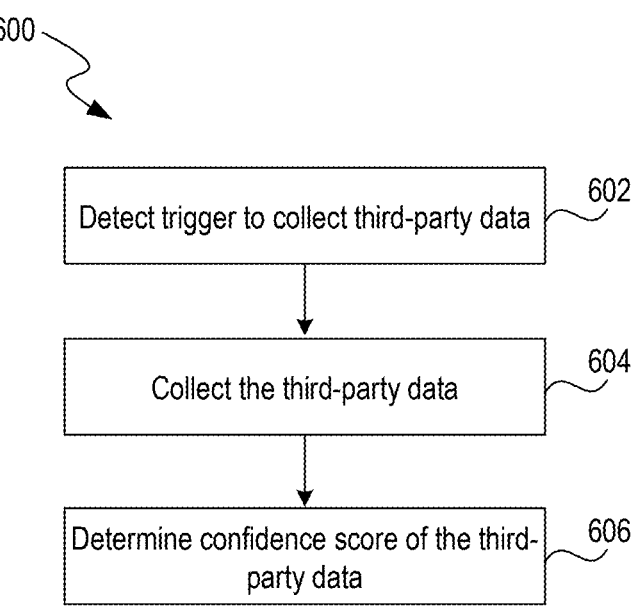
FIG. 6A is a flow diagram illustrating a method for collecting third-party data to provide patient-specific medical care, according to an embodiment.
Figure 7D:
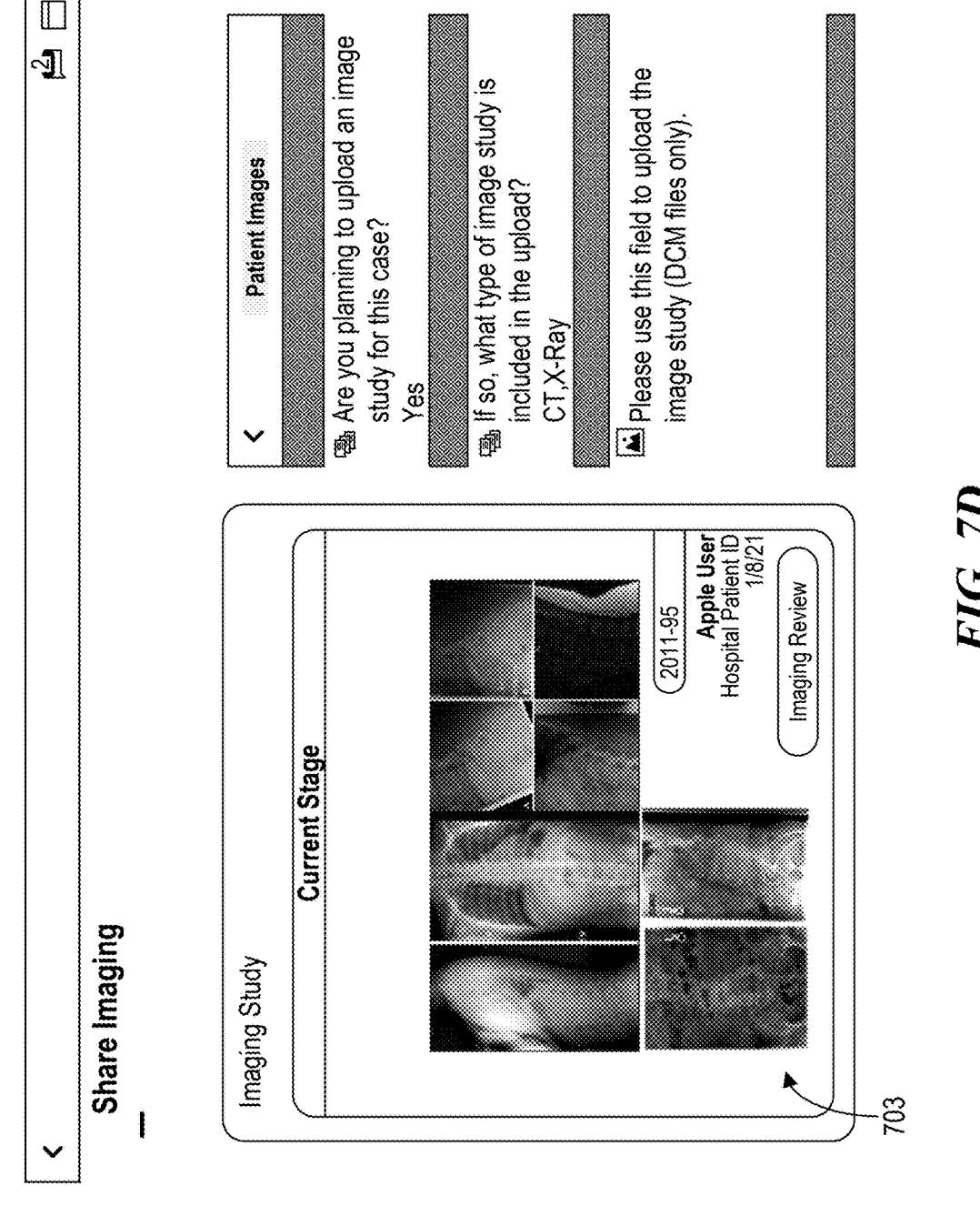

FIG. 6A is a flow diagram illustrating a method 600 for collecting third-party data to provide patient-specific medical care, according to an embodiment. The method 600 can include one or more automated collection protocols for available clinical data for generating surgical plans and implant designs for patients.

At step 602, the system (e.g., computing system 100 of FIG. 1) detects a trigger(s) to collect third-party data for patient treatment. The treatment can include generating surgical plans, implant designs, healthcare goals, recovery plans, or any patient-related activity. A user (e.g., a healthcare provider or a patient) can input trigger controls to select the type of third-party data that is collected. In some embodiments, the trigger is automatically selected by the system based on information of the patient, such as type of disease, age, demographic, surgery type, etc. The trigger can be based on the results of an implant design check performed by the system being below a threshold value. In some embodiments, the implant design check can be performed by a surgeon (as described at steps 508, 510, 512, and 514 of FIG. 5). For example, characteristics (e.g., the size, material, or shape as described in FIG. 1) of the implant design are analyzed to determine whether the implant will cause damage to the anatomy (e.g., soft tissue, vertebrae, etc.) of the patient if installed. Trained machine learning model(s) can determine whether various implant designs (e.g., patient-specific orthopedic implants) are likely to produce a favorable outcome for the patient, or meet one or more parameters (e.g., coverage parameters, reimbursement parameters, regulatory parameters, or the like). Based on these determinations, the trained machine learning model(s) can score an implant design for the patient. In embodiments where multiple trained machine learning models are used, the models can be run sequentially or concurrently to compare outcomes and can be periodically updated using training data sets. Triggers can be modified, added, removed, ranked, scored, or the like by, for example, a user, a system, etc.

The system can perform ranking protocols, checking routines, scoring routines, or other routines. For example, the system can perform one or more of the protocols, routines, or methods on implant designs, plans, etc. U.S. application Ser. No. 18/408,409; U.S. application Ser. No. 16/699,447; U.S. Pat. Nos. 11,083,586; and 11,376,076, which are incorporated by reference in their entireties, disclose technology (e.g., modules, protocols, routines, algorithms, methods, and/or event(s) associated with trigger(s)) that can be part of, or performed by, the system.

In some embodiments, the trigger for the collection of third-party data is based on patient-specific treatment planning. The system can determine that there is insufficient data stored in a database to generate a surgical plan or design an implant for a patient. For example, the system can determine whether there is insufficient data to generate a planned corrected pathology with a quality score/confidence score above a threshold. In some procedures, the system can perform intraoperative simulations based on intraoperatively collected data. The system can then modify treatment plans based on the intraoperative data. If the system determines that there is insufficient data for the intraoperative modification, the system can develop a search that can be completed within an acceptable time frame based on the patient's vital signs. The system can collect data and then generate a modified surgical plan based on the collected data to progress with the surgical procedure. This process can be repeated any number of times to complete the procedure.

In some embodiments, the trigger for the collection of third-party data is based on the patient having an edge case pathology. The system can search the internet for data that is similar to the edge case pathology of the patient. For example, the patient has a rare disease that only exists in a different country. In some embodiments, the trigger for the collection of third-party data is based on the system identifying an edge case pathology via an internet search. The system can add the edge case pathology to a database and use the edge case pathology information for generating surgical plans and implant designs for the patient. Example surgical planning and edge case pathologies are described by U.S. application Ser. No. 18/408,409 entitled "Surgical Planning Platform with Design Checker System," which is incorporated by reference in its entirety. In some embodiments, the trigger for the collection of third-party data is based on medical regulatory management and reimbursement criteria. The system can search the internet for data that is similar to data used for similar procedures based on reimbursements. This ensures that coding can be matched with previously approved coding. U.S. patent application Ser. No. 18/537,600 filed Dec. 12, 2023, and entitled "Medical Regulatory Management and Reimbursement System Discloses Example Technology" and U.S. patent application Ser. No. 18/573,600 are both incorporated by reference in their entireties.

In some embodiments, a new treatment, a new type of implant, and/or a new implant design can trigger the system to collect third-party data. A user (e.g., healthcare provider, patient, implant manufacturer, etc.) can manually select implant design parameters from the third-party data for a patient-specific implant. In some embodiments, the system utilizes a machine learning engine to select implant design parameters from the third-party data for a patient-specific implant. The system can train/retrain the machine learning engine to select third-party data with design parameters that can be used to design a patient-specific implant. The system can use a hybrid of machine learning and user selection to select design parameters.

In some embodiments, multi-modality procedures can trigger the system to collect third-party data. The multi-modality procedures can include decompression procedures, fusion procedures, disc replacement procedures, or any spinal procedure. The system can incorporate relevant cases for integration of third-party data from different databases for correlated treatments. In some embodiments, the detection of newly available data triggers the system to collect third-party data. The newly available data can include new journal articles, white papers, new FDA-approved data, or any newly published/released healthcare data.

At step 604, the system can collect third-party data from the source. The system can collect the third-party data periodically, at user-selected times (e.g., a user-inputted schedule, healthcare provider schedule), or when implant design predicted outcomes are below a threshold score.

At step 606, the system can determine a confidence score of the third-party data, which can be encrypted. The confidence score can be based on the characteristics (e.g., peer-reviewed data, authors of the data, experimental data, patient data, FDA-approved data, raw image data, etc.) of the source of the third-party data. Confidence scores associated with third-party data can include, for example, a high confidence level, a medium confidence level, or a low confidence level. In some embodiments, the confidence levels are determined as numerical values (e.g., 1, 5, 67, or any number) or as a percentage (e.g., 26%, 83%, or any percentage). Examples of high confidence level data can include raw image data (e.g., X-rays, MRI images, body scans, etc.), peer-reviewed journal articles or publications on a subject matter associated with the patient, or articles written by selected authors (e.g., authors at prestigious medical institutions, whitelisted authors, etc.). Examples of medium confidence level data can include non-peer-reviewed journal articles, whitelist/blacklist sources based on prior use, validation, or user input. Whitelist/blacklist, multi-factor authentication routines, and/or authentication protocols can be used to authenticate third-party data sources. Examples of low confidence level data can include social media, professional media, sharing websites, or images. The images (e.g., shared via social media) can be analyzed with or without physician descriptions, notes, or treatment outcomes.

The system can determine the confidence score based on the amount of third-party data, the confidence level associated with the data, or the type of data (e.g., images, articles, journals, metrics, etc.). In some embodiments, the score is based on the number of features in the third-party data that match features in the patient's data. The confidence score can increase if the activity level of the patient or the diet/health rating of the patient matches the activity level or diet/health rating of the third-party data. The system can modify the confidence scoring and confidence levels over time as third-party data sources are used and the system approves all or some of the data as legitimate. In some embodiments, the system can partition third-party data into subsets of data. The system can then individually score the partitioned data. This allows for confidence scoring of different portions of data from the same data source. By way of example, a journal article may include patient images, patient measurements, observations, and author conclusions. The system can generate confidence scores separately for the different types of data. In some score routines, high confidence level scores can be based on patient images whereas low confidence level scores can be based on an author's general conclusions.

Figure 6B:
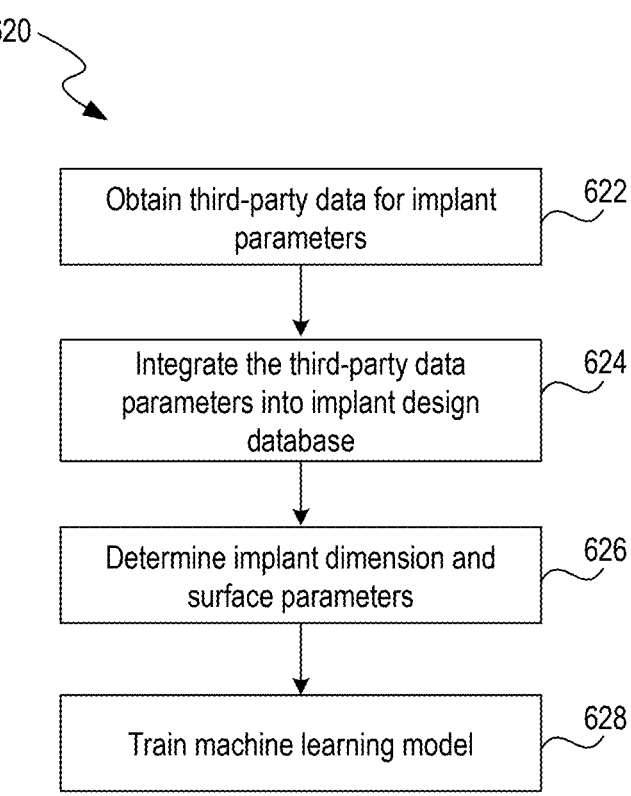
FIG. 6B is a flow diagram illustrating a method for determining outcome-driven parameters for implant design and treatment.

FIG. 6B is a flow diagram illustrating a method 620 for determining outcome-driven parameters for implant design and treatment. The method 620 can include automated collection protocols for available clinical data for generating surgical plans and implant designs for patients.

At step 622, the system can obtain third-party data for implant parameters. The third-party data can be selected and collected according to steps 602-606 of FIG. 6A.

At step 624, the system can integrate the third-party data parameters into an implant design database, treatment planning database, surgical technique database, or another database. The system can analyze user-specific (e.g., healthcare provider, implant designer, or patient) treatments and/or standard implant treatments in the third-party data and integrate the third-party data parameters into a database to design a patient-specific implant for the patient.

At step 626, the system can determine implant dimension and surface parameters. The system can store metadata or parameters for patient population. The surface parameters can include minimum and maximum load-bearing areas, texturing of the implant, contours of the implant, or any surface features of the implant. The system can determine manufacturing techniques based on the determined implant dimensions and surface parameters. The system can determine reciprocal changes or disease progression for a patient based on the third-party data parameters.

At step 628, the system can train/retrain a machine learning model based on the third-party data collection triggers, confidence scoring, or selected third-party data parameters. The system can determine design constraints based on FDA requirements or design constraints based on implant testing.

Figure 6C:
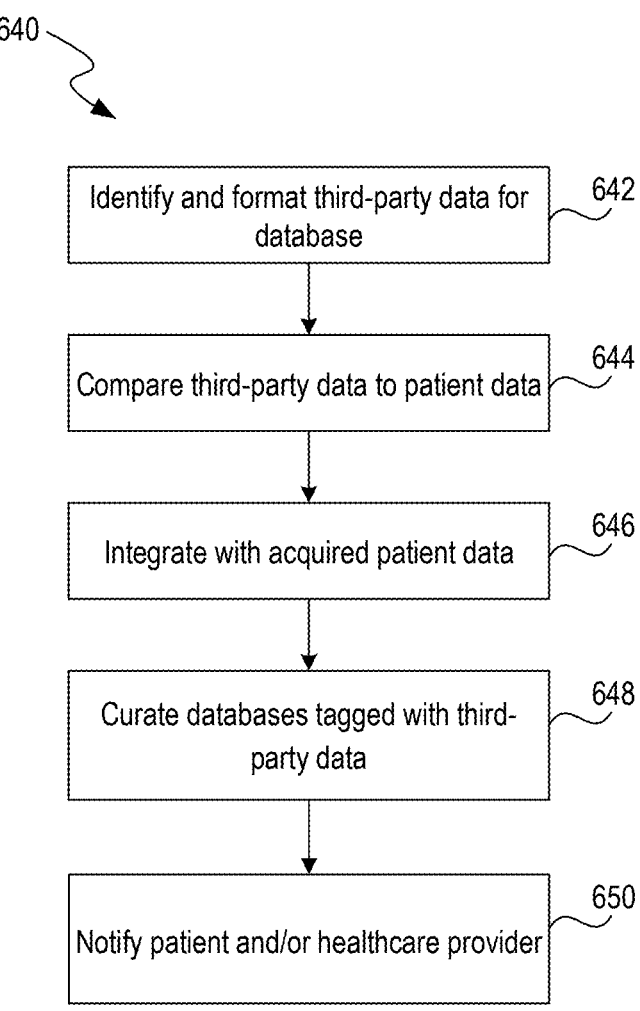
FIG. 6C is a flow diagram illustrating a method for managing patient data to provide patient-specific medical care, according to an embodiment.

FIG. 6C is a flow diagram illustrating a method 640 for managing patient data to provide patient-specific medical care, according to an embodiment. The method 640 can include automated collection protocols for available clinical data for generating surgical plans and implant designs for patients.

At step 642, the system can identify, collect, curate, and/or format third-party data for a database.

At step 644, the system can compare the third-party data to patient data and select similar data based on the comparison. The system can identify similar third-party data to use for simulations to predict one or more outcomes of installing an implant in a patient.

At step 646, the system can integrate the selected data with acquired patient data stored in the database(s). For example, the system matches the selected data with similar data in the database. The system can build treatment databases, patient type databases, and/or implant design databases. In some embodiments, the system can tag databases that include selected third-party data.

At step 648, the system can curate databases tagged with third-party data. As new third-party data is collected or the data is evaluated, the system can remove or replace third-party data with new or alternative data. The system can free up memory storage in databases or user devices by removing any unselected third-party data. The system can remove third-party data after the data is analyzed or incorporated into the treatment of a patient.

At step 650, the system can notify the healthcare provider and/or the patient of selected third-party data that can be used for designing an implant or treatment of a patient. The system can notify the healthcare provider or patient of new clinical data with a notification (e.g., alert, message, etc.). The notification can include a link to data sources (e.g., social media, a database, website, etc.) or a citation of the source of the third-party data. The system can upload the selected third-party data as a new data set for user (e.g., healthcare provider or patient) review. In some embodiments, the system can display the third-party data in a user interface for the healthcare provider or patient to view. The user interface (GUI) can display similarities and differences between the third-party data and the patient data. The user can select and edit any of the third-party data. GUIs displaying of third-party data driven treatment plans, third-party data, displayed data, or the like are discussed in connection with FIGS. 10A-10C.

Machine learning algorithms can be used to perform one or more steps of method 600 of FIG. 6A, method 620 of FIG. 6B, or method 640 of FIG. 6C. For example, the TPC platform 109 of FIG. 1 can include a machine learning model trained using the selected third-party data sets. The third-party data can be inputted into the trained machine learning model to identify data similar to the patient data. The machine learning model can be selected based on implant design goals or patient treatment goals.

FIGS. 7A-13 further illustrate select aspects of providing patient-specific medical care, e.g., in accordance with the method 500. For example, FIGS. 7A-7D illustrate an example of a patient data set 700 (e.g., as received in step 502 of the method 500). The patient data set 700 can include any of the information previously described with respect to the patient data set. For example, the patient data set 700 includes patient information 701 (e.g., patient ID, patient medical record number, patient name, sex, age, BMI, surgery date, surgeon, etc., shown in FIGS. 7A and 7B), diagnostic information 702 (e.g., Oswestry Disability Index (ODI), VAS-back score, VAS-leg score, pre-operative pelvic incidence, pre-operative lumbar lordosis, pre-operative PI-LL angle, pre-operative lumbar coronal Cobb, etc., shown in FIGS. 7B and 7C), and image data 703 (X-ray, CT, MRI, etc., shown in FIG. 7D). In the illustrated embodiment, the patient data set 700 is collected by a healthcare provider (e.g., a surgeon, a nurse, etc.) using a digital and/or fillable report that can be accessed using a computing device. In some embodiments, the patient data set 700 can be automatically or at least partially automatically generated based on digital medical records of the patient. Regardless, once collected, the patient data set 700 can be transmitted to the computing system configured to generate the surgical plan for the patient.

Figure 8A:
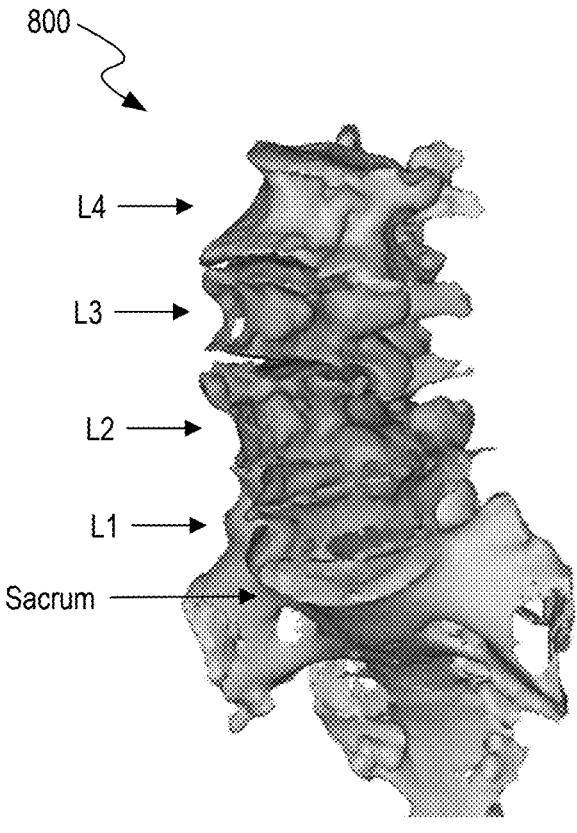
FIGS. 8A and 8B illustrate an exemplary virtual model of a patient's spine that may be used and/or generated in connection with the methods described herein, according to an embodiment.
Figure 8B:
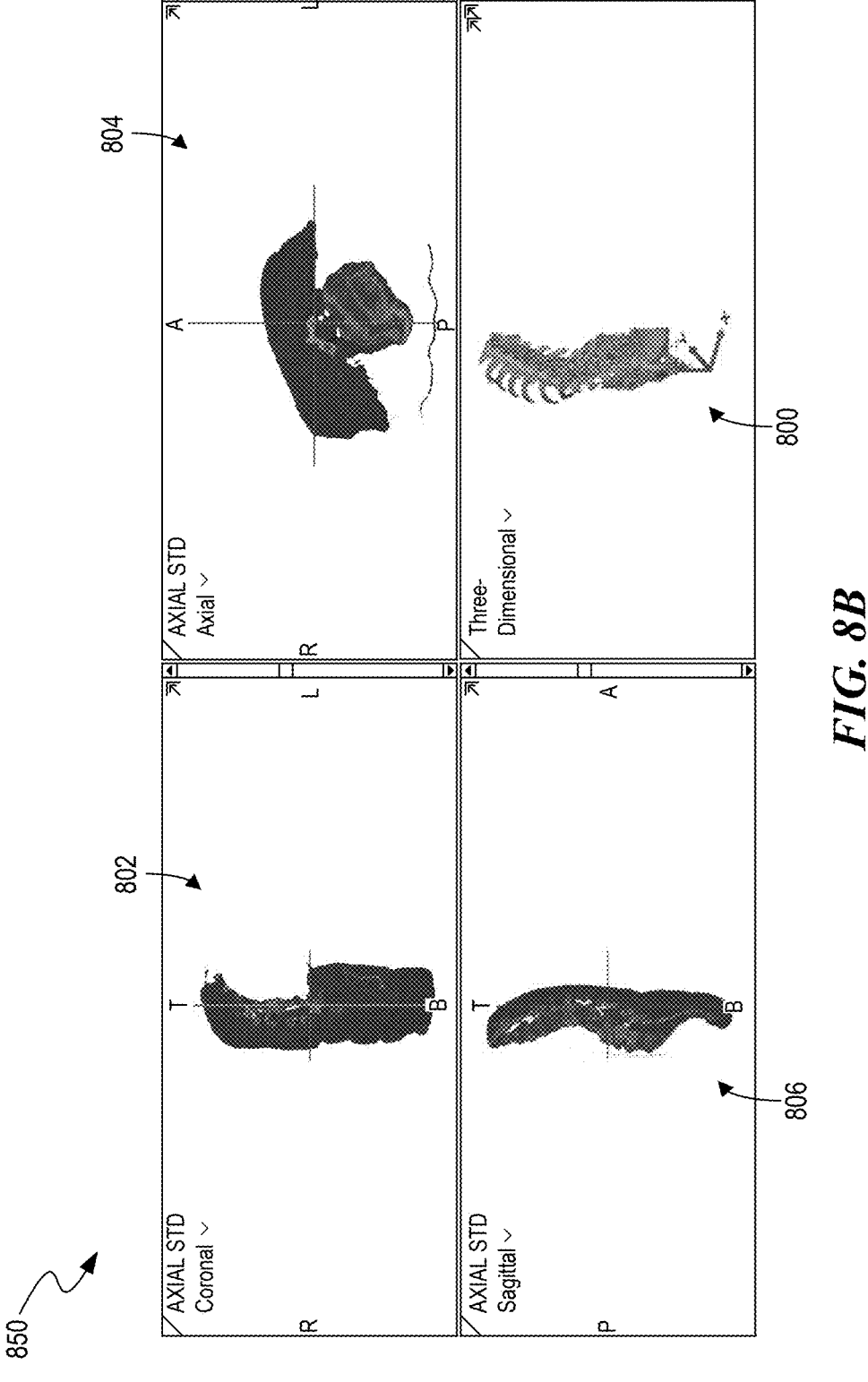

FIGS. 8A and 8B illustrate an example of a virtual model 800 of a patient's native anatomical configuration (e.g., as created in step 503 of the method 500). In particular, FIG. 8A is an enlarged view of the virtual model 800 of the patient's native anatomy and shows the patient's native anatomy of their lower spinal cord region. The virtual model 800 is a 3D visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 800 only includes bony structures of the patient's anatomy, but in other embodiments may include additional structures, such as cartilage, soft tissue, vascular tissue, nervous tissue, etc.

FIG. 8B illustrates a virtual model display 850 (referred to herein as the "display 850") showing different views of the virtual model 800. The virtual model display 850 includes a 3D view of the virtual model 800, one or more coronal cross-section(s) 802 of the virtual model 800, one or more axial cross-section(s) 804 of the virtual model 800, and/or one or more sagittal cross-section(s) 806 of the virtual model 800. Of course, other views are possible and can be included on the virtual model display 850. In some embodiments, the virtual model 800 may be interactive such that a user can manipulate (e.g., rotate) the orientation or view of the virtual model 800, change the depth of the displayed cross-sections, select and isolate specific bony structures, or the like.

Figures 1, 2, 9A:
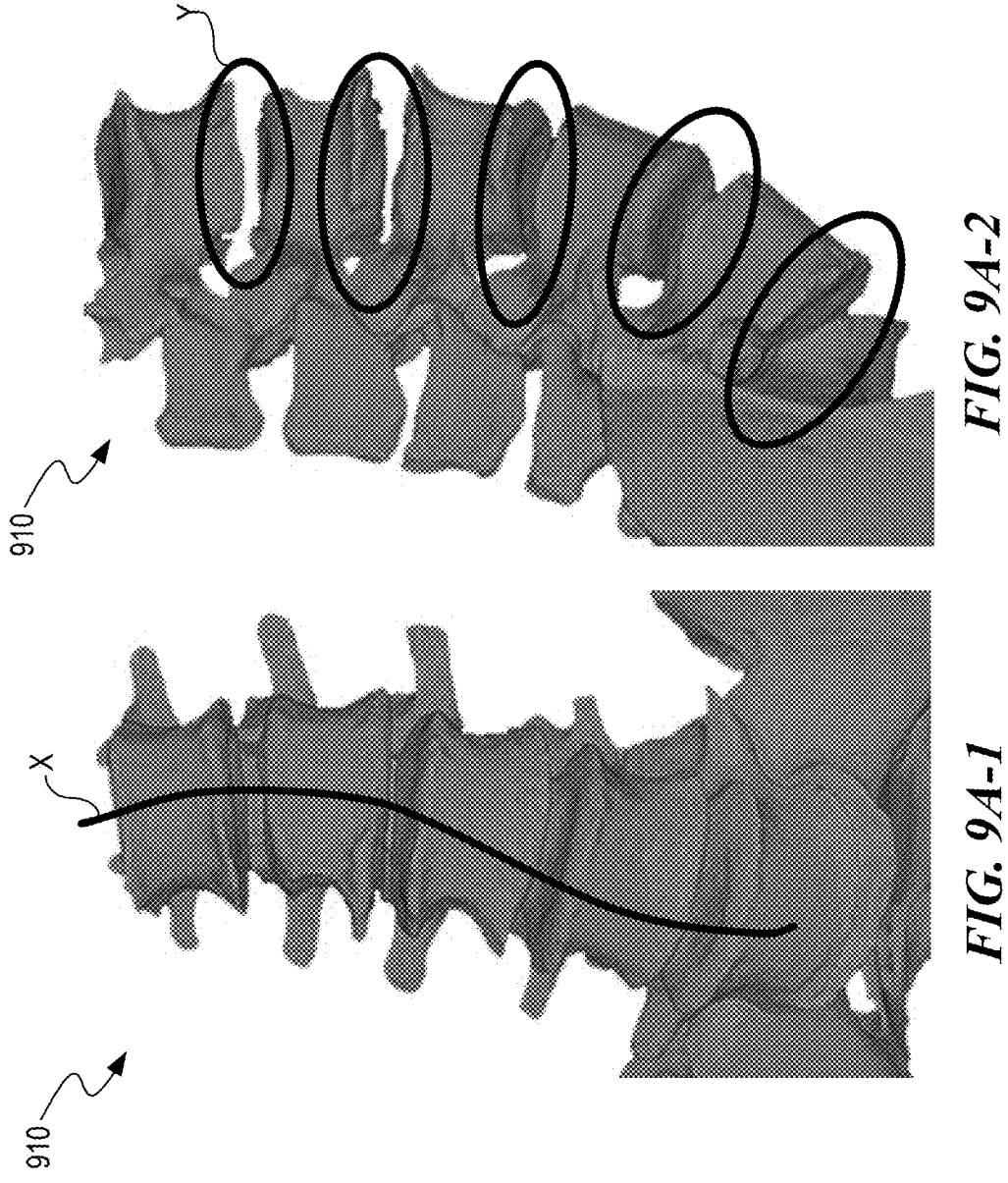
Figures 1, 2, 9B:
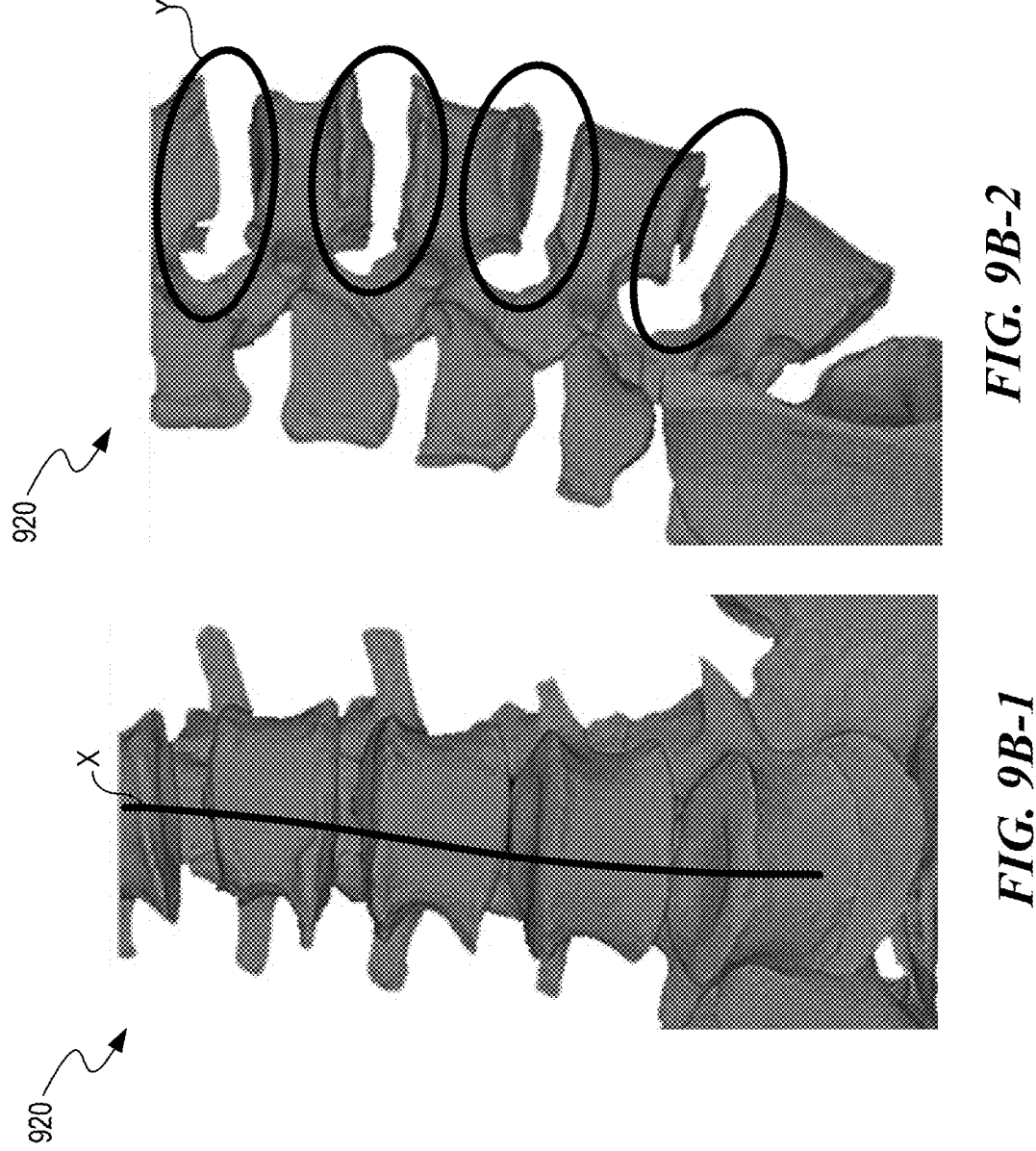

FIGS. 9A-1-9B-2 demonstrate an example of a virtual model of a patient's native anatomical configuration (e.g., as created in step 503 of the method 500) and a virtual model of the patient's corrected anatomical configuration (e.g., as created in step 504 of the method 500). In particular, FIGS. 9A-1 and 9A-2 are anterior and lateral views, respectively, of a virtual model 910 showing a native anatomical configuration of a patient, and FIGS. 9B-1 and 9B-2 are anterior and lateral views, respectively, of a virtual model 920 showing the corrected anatomical configuration for the same patient. Referring first to FIG. 9A-1, the anterior view of the virtual model 910 illustrates that the patient has abnormal curvature (e.g., scoliosis) of their spinal column. This is marked by line X, which follows a rostral-caudal axis of the spinal column. Referring next to FIG. 9A-1, the lateral view of the virtual model 910 illustrates that the patient has collapsed discs or decreased spacing between adjacent vertebral endplates, marked by ovals Y. FIGS. 9B-1 and 9B-2 illustrate the corrected virtual model 920 accounting for the abnormal anatomical configurations shown in FIGS. 9A-1 and 9A-2. For example, FIG. 9B-1, which is an anterior view of the virtual model 920, illustrates the patient's spinal column having corrected alignment (e.g., the abnormal curvature has been reduced). This correction is shown by line X, which also follows a rostral-caudal axis of the spinal column. FIG. 9B-2, which is a lateral view of the virtual model 920, illustrates the patient's spinal column having restored disc height (e.g., increased spacing between adjacent vertebral endplates), also marked by ovals Y. The lines X and the ovals Y are provided in FIGS. 9A-1-9B-2 to more clearly demonstrate the correction between the virtual models 910 and 920, and are not necessarily included on the virtual models generated in accordance with the present technology.

Figure 10A:
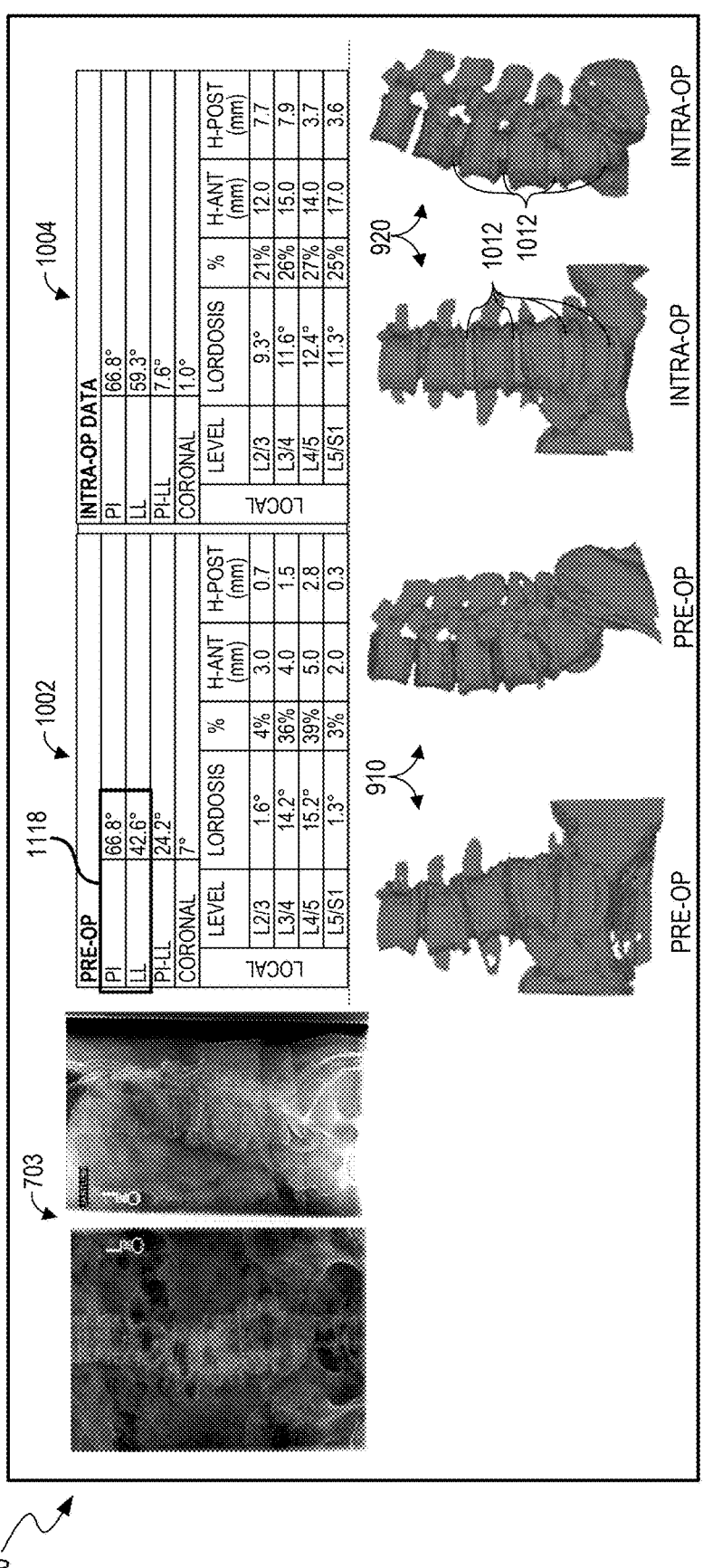
FIG. 10A illustrates an exemplary interactive surgical plan for a patient-specific surgical procedure, according to an embodiment.

FIG. 10A illustrates an example of a surgical plan 1000 (e.g., as generated in step 506 of the method 500, method 600 of FIG. 6A, or method 620 of FIG. 6B). The surgical plan 1000 can include pre-operative patient metrics or measurements 1002, intra-operative patient metrics 1004, one or more patient images (e.g., the patient images 703 received as part of the patient data set), the virtual model 910

(which can be the model itself or one or more images derived from the model) of the patient's native anatomical configuration (e.g., pre-operative patient anatomy), and/or the intra-operative virtual model 920 (which can be the model itself or one or more images derived from the model) of the patient's corrected anatomical configuration (e.g., intra-operative patient anatomy). The pre-operative patient metrics 1002 can include, without limitation, lumbar lordosis, Cobb angle(s), pelvic incidence, disc height, coronal offset distance, segment flexibility, LL-PI greater than a predetermined number of degrees (e.g., 5 degrees, 10 degrees, etc.), LL-PI mismatch (e.g., age-adjusted), sagittal vertical axis offset distance, coronal offset distance, coronal angle, bone quality, and/or rotational displacement.

The virtual model 920 of the intra-operative patient anatomy can optionally include one or more implants 1012 shown as implanted in the patient's spinal cord region to demonstrate how patient anatomy will look following the surgery. Although four implants 1012 are shown in the virtual model 920, the surgical plan 1000 may include more or fewer implants 1012, including one, two, three, five, six, seven, eight, or more implants 1012.

The surgical plan 1000 can include additional information beyond what is illustrated in FIG. 10A. For example, the surgical plan 1000 may include pre-operative instructions, operative instructions, and/or post-operative instructions. Operative instructions can include one or more specific procedures to be performed (e.g., PLIF, ALIF, TLIF, LLIF, DLIF, XLIF, etc.) and/or one or more specific targets of the operation (e.g., fusion of vertebral levels L1-L4, anchoring screw to be inserted in lateral surface of L4, etc.). Although the surgical plan 1000 is demonstrated in FIG. 10A as a visual report, the surgical plan 1000 can also be encoded in computer-executable instructions that, when executed by a processor connected to a computing device, cause the surgical plan 1000 to be displayed by the computing device. In some embodiments, the surgical plan 1000 may also include machine-readable operative instructions for carrying out the surgical plan. For example, the surgical plan can include operative instructions for a robotic surgical platform to carry out one or more steps of the surgical plan 1000.

Figure 10B:
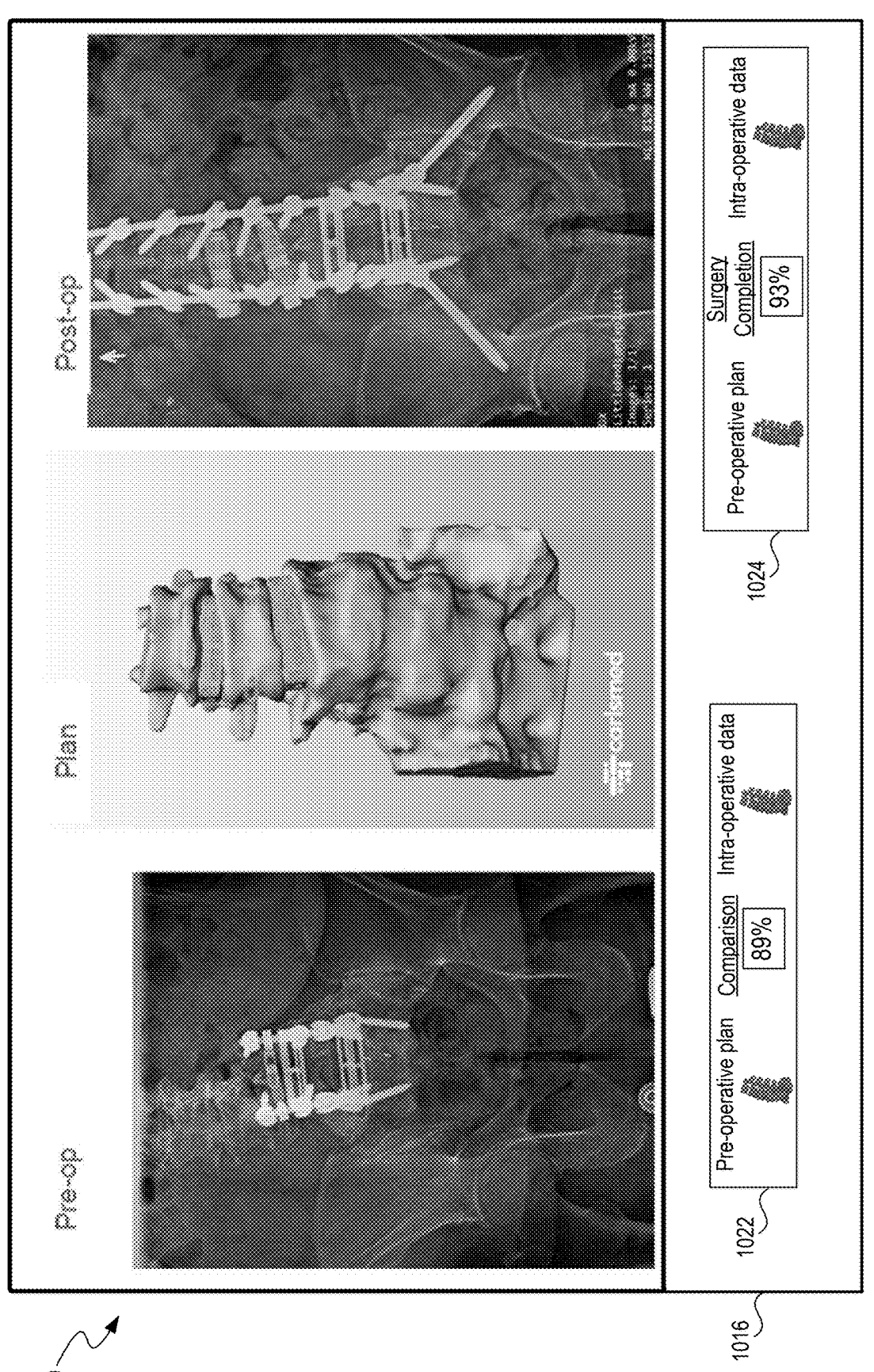
FIG. 10B illustrates pre-operative, plan, intra-operative, and post-operative images to allow for assessment of achievement of surgical goals, according to an embodiment.

FIG. 10B illustrates plan 1020 with a pre-operative image, pre-operative plan, intra-operative image, and post-operative image to allow for assessment of achievement of surgical goals, according to an embodiment. Plan 1020 can display a notification 1022 of a comparison percentage (e.g., 89%) of the intra-operative data to the pre-operative plan. Plan 1020 can display notification 1024, which is a metric of completion (e.g., 93%) of the installation of the implant in the patient. The pre-operative plan images can be generated based on one or more pre-operative images, virtual models (e.g., 3D virtual models), and/or other data disclosed herein. The data can be manipulated or modified to, for example, compensate for loading conditions by, for example, repositioning features in the virtual model to match intra-operative loading conditions. The planned image of FIG. 10B shows planned positions for anatomical elements of the patient. The planned image can also include additional features from the pre-operative image, such as the fixation system in the illustrated pre-operative image. The previously implanted fixation system can be used in the landmark for aligning the intra-operative images and the planned images.

Figure 10C:
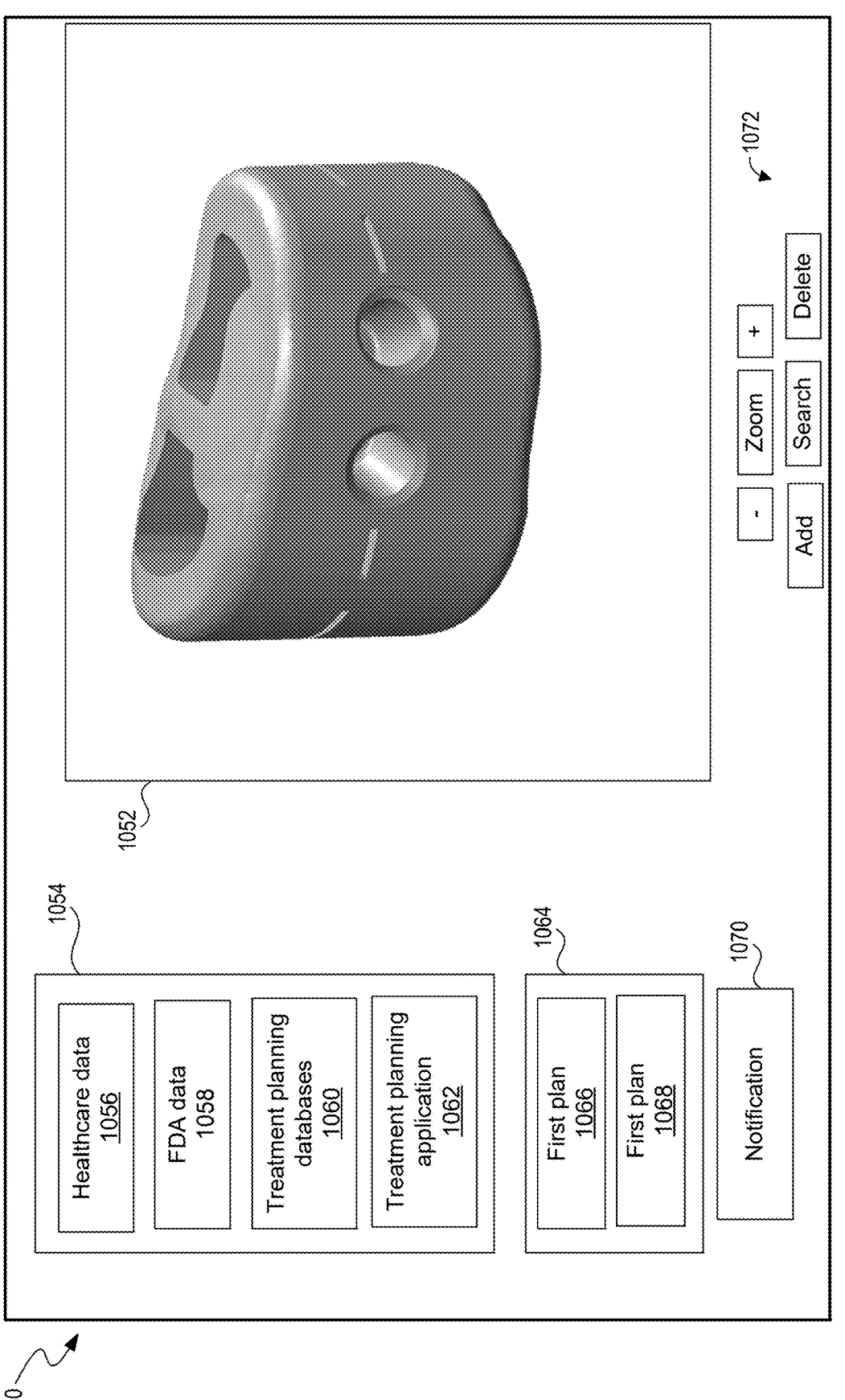
FIG. 10C illustrates a graphical user interface (GUI) for visually depicting various aspects of third-party data, according to an embodiment.

FIG. 10C illustrates an example GUI 1050 for visually depicting various aspects of third-party data, including similarities or differences in comparison to data of the patient. The GUI can be displayed by devices (e.g., device 122 of FIG. 1) to manage third-party data used in methods 500 of FIG. 5, method 600 of FIG. 6A, and/or method 620 of FIG. 6B to generate surgical plans (e.g., surgical plan 1000 of FIG. 10A, surgical plan 1020 of FIG. 10B, etc.). The GUI 1050 can dynamically combine information from multiple sources and/or data generated based on information from multiple sources. The GUI can include various icons/elements 1054-1072 that when selected access various types of data, databases, applications, implant design plans, notifications, etc.

The GUI 1050 can display available third-party data sources 1054 (e.g., healthcare data 1056 and FDA approved data 1058) selectable using one or more selector boxes, menus, etc. for selecting or deselecting the sources (e.g., selecting for detailed review of third-party data), selecting items show in a display or window 1052, or the like. The GUI 1050 can then display third-party data from user-selected sources and a set of the third-party data used to generate surgical plans. This allows a user to navigate available data sources that are trusted by the user. The GUI 1050 can have alignment selectors for aligning pre-operative model (e.g., virtual 3D model), images (e.g., images of virtual models), anatomical renderings, or other images displaying anatomical position information on the device. In some cases, a user can zoom, stretch, and/or rotate the virtual 3D model (or other pre-operative images) to align with the intra-operative image on the device or other viewing platform, search models or plans, add items, or delete items. The items can be data sets, features of implants displayed in the window 1052, third-party sources (e.g., third-party sources 1054), plans (e.g., plans 1064), etc.

The GUI 1050 can display the third-party sources 1054 selected for continuous or periodic queries. If the third-party sources 1054 are updated, the system can automatically search the third-party data source to determine whether newly available sources or data should be used. A notification can be sent to or displayed to the user if one or more of the third-party data sources become unavailable. The user can select a notification button 1070 to set notification settings (e.g., when to notify, how to notify, etc.).

In some embodiments, the GUI 1050 can allow the user to select or deselect sets of data. If the user deselects a set of third-party data (e.g., a set of data based on a particular population group), a treatment plan can be updated without using the deselected third-party data. In some embodiments, the GUI 1050 can show different treatments based on whether third-party data sets or sources are used. In some embodiments, the user can select or deselect types of data (e.g., images, text, reference patient data, data from studies, etc.) to be collected, utilized, or the like. In some embodiments, the user or system can select sets of metrics/parameters from treatment plans to generate a new treatment plan for achieving the selected metrics/parameters.

The GUI can also include one or more controls 1072 for selecting or deselecting sets of data, for controlling receiving, collecting, searching, and/or managing data from remote or third-party applications or programs, managing implant design, viewing and modifying surgical plans, or the like. In some embodiments, the system can identify candidate third-party data sources with available data for treatment planning. For example, a user can select one or more available treatment planning databases 1060, treatment planning applications 1062, on remote servers, and those selected databases and/or applications can generate treatment plans 1064, which can be consolidated into a single plan. In some embodiments, the GUI can display a first plan 1066 for intervertebral cages manufactured by a first manufacture. The GUI can concurrently or sequentially display a second plan 1068 for instruments or surgical equipment from a second manufacture. The GUI can show a single surgical procedure plan with post-operative outcomes associated with the first and/or second plans. The GUI 1050 can automatically update data (e.g., simulation data, predicted outcomes, etc.) based on newly available data acquired before, during, and/or after a surgical procedure. The GUI 1050 can visually identify deviations between data based on the prior data and the newly available data.

To facilitate visualization, the GUI 1050 can display one or more patient images, virtual models, and associated metrics/parameters, including pre-operative metrics/parameters, planned metrics/parameters, and/or post-operative metrics/parameters. Example images, virtual models, and associated metrics/parameters, including pre-operative metrics/parameters, planned metrics/parameters, and/or post-operative metrics/parameters are discussed in connection with FIG. 10A-10B. The data can be automatically scaled or manipulated (e.g., cropped, enlarged, processed, etc.) to show features of interest at suitable sizes (e.g., visually identifiable sizes), viewing perspectives, etc. The GUI 1050 can automatically receive additional data based on the displayed data and viewing by the user. In response to a user zooming to view specific region(s) of a virtual model, the system can retrieve additional third-party data associated with the specific region(s). In response to the user inputting non-conforming implant positions, non-conforming metrics, etc., the system can obtain third-party for providing information about predicted outcomes and/or adverse events (e.g., intra-operative adverse events, impaired post-operative recovery, etc.) associated with the non-conforming inputs. Non-conforming inputs can be identified using one or more checkers, simulators, etc.

As another example, the GUI 1050 can show a design for a medical device to be implanted in the patient, such as a 2D or 3D model of the device design. The user can use an input device (e.g., touch screen, console for a surgical robot, etc.) to select features of the implant. The GUI 1050 can automatically display dimensions of and/or information about the selected feature. The device design can include, for example, a size and configuration of an implant (e.g., footprint of intervertebral cage), length and curvature of spinal rods, length and characteristics of screws (e.g., bone screws, pedicle screws), range of motion of artificial discs, or the like. The display 1052 can also show patient information, such as 2D or 3D images or models of the patient's anatomy where the surgical procedure is to be performed and/or where the device is to be implanted. In some procedures, the system can design implants based on received third-party data related to the size of the implant. For example, the size of the implant (e.g., an interbody cage or an artificial disc) can be a percentage of vertebral endplate(s), percentage of original disc height prior to surgery, or the like. In some procedures, the system can design implants based on received third-party data related to the curvature of the patient's spine. For example, a length, curvature, porosity, and strength of the implants (e.g., spinal rods) can be designed based on the received third-party data (e.g., mechanical strength data, curvature data, porosity and bone growth data, etc.).

The GUI 1050 can display recommended treatments, surgical techniques, types of implants, procedures (e.g., levels of treatment in spine procedures), implantation data, placement criteria, contact interface criteria, loading criteria, properties of implants, characteristics of implants, or the like. The GUI 1050 can automatically rearrange data, buttons, image windows, or other displayed items on a screen based on ranking, scoring (e.g., reliability scores, predicted impact on outcome scores, etc.), user usage, and/or rules (e.g., user inputted rules, ML/AI generated rules, etc.). In spine procedures, the type of implant can be, for example, a fixed intervertebral cage, an artificial disc, a rod (e.g., spinal rod), posterior fixation element, etc. selected based on whether the system determines there should be mobility at spinal levels, fusion at spinal levels, etc. The placement criteria can include, for example, distance from anatomical features, position with respect to the perimeter of a vertebral endplate or body, and/or other positional location. In some spinal fusion procedures, the coverage criteria can include, for example, maximum or minimum percentage of coverage of the vertebral endplate, areas of coverage along the vertebral endplate, or the like. The load-bearing characteristics can include, for example, strength of the implant, fracture toughness of the implant, fatigue life of implant, degrees of motion of the implant, or the like. The characteristics of the implant can include, for example, lattice characteristics (e.g., density of lattice structure, distribution of lattice structure), openings for receiving grafting material, medicants, bone growth material (e.g., demineralized bone matrix (DBM), bone morphogenetic protein (BMP), etc.), bone cement, combinations of materials, or the like. The display 1052 can display recommendations for other procedures.

The GUI 1050 can have a customized layout and may include functionality for receiving user selections to organize displayed elements based on specific criteria, such as the amount of use of each icon or data source. The layout can be a physician-specific layout, treatment-specific layout, or other layout. A user may interact with the control panel 1072 to specify organizing the available treatment planning databases 1060, treatment planning applications 1062, or other data sources 1054 based on their frequency of access or utilization. The system may then determine the amount of use for each icon or data source by tracking metrics such as memory allocation, processing time, or access frequency over a predetermined period using the underlying computing resources.

Based on this usage analysis, the GUI 1050 may automatically rearrange the positioning of icons, data sources, or other interface elements to optimize user workflow. For instance, the most frequently used treatment planning databases 1060 or applications 1062 may be moved to prominent positions near the top of the data window 1054 or adjacent to commonly accessed controls. Similarly, frequently referenced healthcare data 1056 or FDA data 1058 sources may be prioritized in the display order. This dynamic reorganization of the GUI 1050 based on usage patterns may help streamline navigation and improve efficiency when working with complex treatment planning workflows involving multiple data sources and applications.

The graphical user interface (GUI) 1050 may provide a standardized platform for storing and accessing information (e.g., surgical plans, patient information, etc.) across a network of storage devices. The data window 1054 can display available third-party data sources such as healthcare data 1056 and FDA approved data 1058, allowing users to select relevant information to be incorporated into a patient's medical record. This centralized system enables storage of patient condition data in a consistent format across multiple networked storage locations, facilitating efficient retrieval and analysis.

Users may remotely access and update patient information through the GUI 1050 in real-time, regardless of their specific hardware or software setup. The control panel 1072 provides interface controls for managing displayed data, allowing users to add, search, or modify information about a patient's condition. When updates are made through the GUI 1050, the system may automatically convert non-standardized inputs into a standardized format before storing the information in the centralized medical record database. This ensures data consistency while accommodating various user platforms.

The notification module 1070 may be utilized to automatically generate and transmit messages to all authorized users whenever patient information is updated in the system. Users can customize notification settings to specify how and when they receive alerts about new patient data. By leveraging the real-time capabilities of the GUI 1050, including features like the treatment planning databases 1060 and applications 1062, all or some of the users (e.g., primary medical team, specialist, family members, etc.) can maintain immediate access to the most current patient information. This facilitates collaborative care and informed decision-making across the healthcare team.

Figure 11:
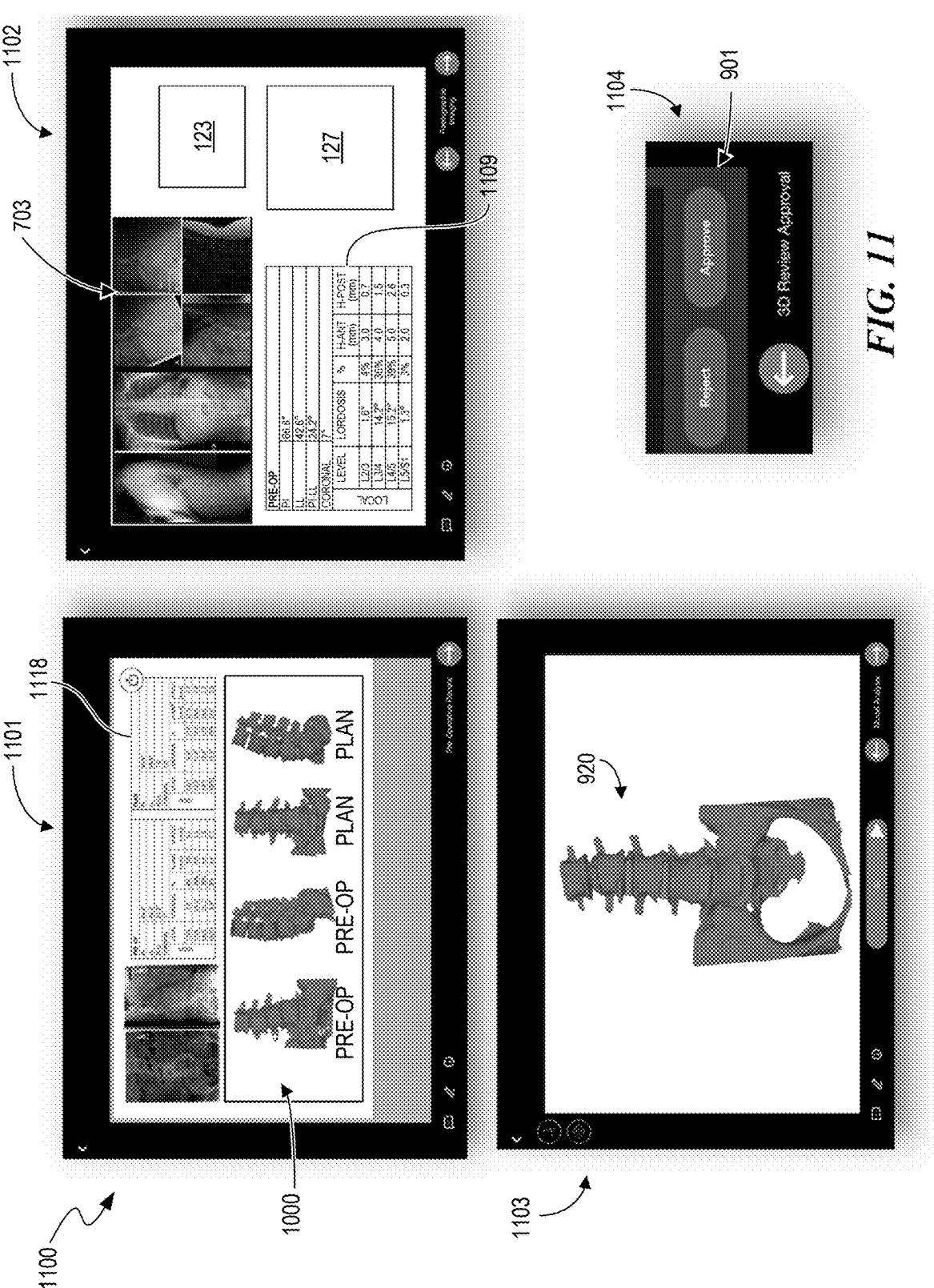
FIG. 11 illustrates an exemplary surgical plan report that details the surgical plan for surgeon review and that may be used and/or generated in connection with the methods described herein, according to an embodiment.

FIG. 11 provides a series of images illustrating an example of a patient surgical plan report 1100 that includes the surgical plan 1000 and that may be transmitted to a surgeon for review and approval (e.g., as transmitted in step 508 of the method 500). The surgical plan report 1100 can include a multi-page report detailing aspects of the surgical plan 1000. For example, the multi-page report may include a first page 1101 demonstrating an overview of the surgical plan 1000 (e.g., as shown in FIG. 10A), a second page 1102 illustrating patient images (e.g., such as the patient images 703 received in step 502 and shown in FIG. 7D), a third page 1103 illustrating an enlarged view of the virtual model of the corrected anatomical configuration (e.g., the virtual model 920 shown in FIGS. 9B-1 and 9B02, and a fourth page 1104 prompting the surgeon to either approve or reject the surgical plan via a user input element 901 (e.g., one or more buttons, a drop-down menu, etc.). The surgical plan report 1100 can include one or more pre-operative metrics for pre-determined indications.

The second page 1102 can include pre-operative metrics 1109 determined based on the patient images 1113. The pre-operative metrics 1109 can be used to perform a reimbursement analysis, including whether a procedure, kit, instrument, implants, or other treatment-related item or step will qualify for payment or reimbursement. In some embodiments, planned metrics 1118 (first page 1101) can be used to validate a predicted outcome for the pre-determined indications that will qualify for payment or reimbursement.

The second page 1102 can also include reimbursement data 123 and regulatory data 127. The reimbursement data 123 can include the data discussed in connection with FIG. 10B. The output (e.g., recommended codes) can be labeled in the illustrated images 703. The pre-operative metrics 1109 correlated to the coding can be bolded or otherwise identified. This allows a user to simultaneously view reimbursement information and physiology associated with those reimbursements. The regulatory data 127 can include images of virtual models with anatomical features and regulatory compliant implants. The planned anatomical model (e.g., virtual model 920 of FIG. 10A) can have implants with regulatory approved configurations. The physician can therefore have confidence that the implants and planned outcome are based on regulatory approved technology.

In some embodiments, the system can measure the anatomical features and generate virtual models. The system can then generate the regulatory compliant implants that fit the model. If the physician modifies the model or implants resulting in a non-regulatory compliant treatment or implant, the system can generate an alert indicating that regulatory compliance has not been maintained. Advantageously, the second page 1102 allows a user to simultaneously view patient images, anatomical planned models, planned pathologies based on regulatory compliance, reimbursement data, and regulatory data. Moreover, correlations between various elements of different data sets can be identified to enable a viewer to understand the interrelationships.

Of course, additional information about the surgical plan can be presented with the report 1100 in the same or different formats. In some embodiments, if the surgeon rejects the surgical plan 1000, the surgeon can be prompted to provide feedback regarding the aspects of the surgical plan 1000 the surgeon would like adjusted.

The patient surgical plan report 1100 can be presented to the surgeon on a digital display of a computing device (e.g., the client computing device 102 shown in FIG. 1). In some embodiments, the report 1100 is interactive and the surgeon can manipulate various aspects of the report 1100 (e.g., adjust views of the virtual model, zoom in, zoom out, annotate, etc.). However, even if the report 1100 is interactive, the surgeon generally cannot directly change the surgical plan 1000. Rather, the surgeon may provide feedback and suggested changes to the surgical plan 1000, which can be sent back to the computing system that generated the surgical plan 1000 for analysis and refinement.

Figure 12A:
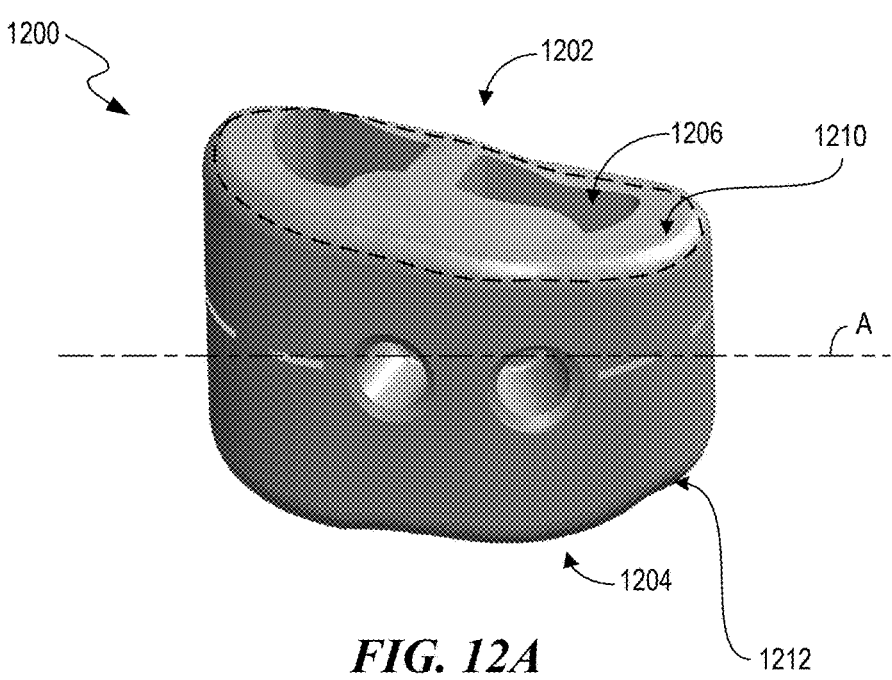
FIGS. 12A and 12B illustrate an exemplary patient-specific implant that can be used and/or generated in connection with the methods described herein, according to an embodiment.
Figure 12B:
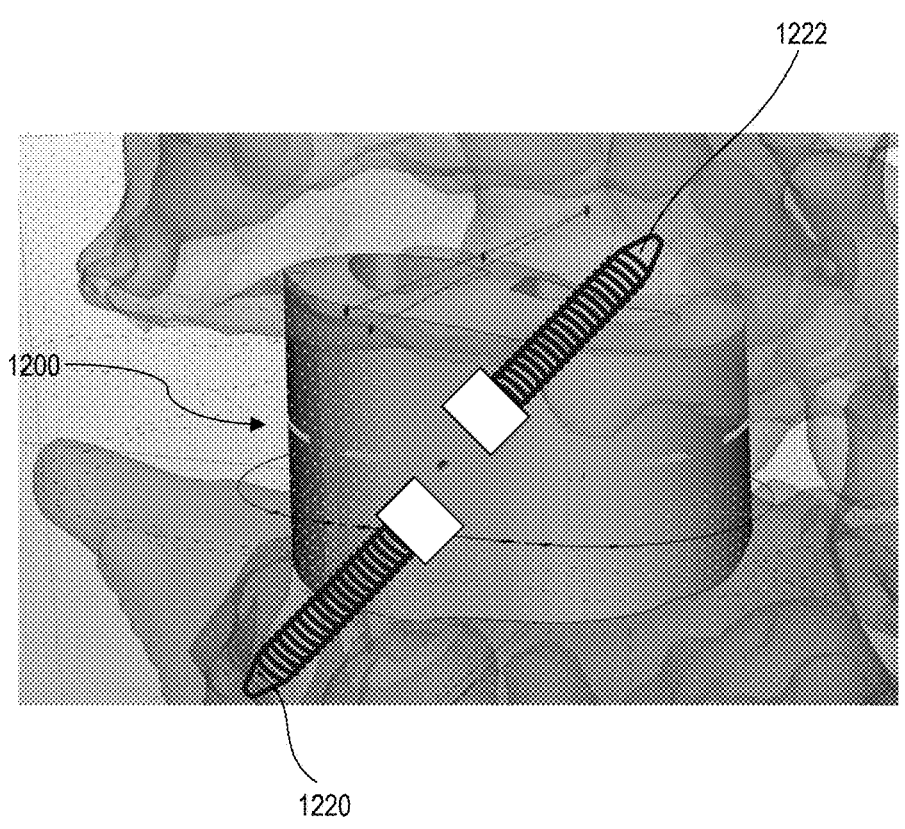

FIG. 12A illustrates an example of a patient-specific implant 1200 (e.g., as designed in step 516 and manufactured in step 518 of the method 500), and FIG. 12B illustrates the implant 1200 implanted in the patient. The implant 1200 can be any orthopedic or other implant specifically designed to induce the patient's body to conform to the previously identified corrected anatomical configuration. The implant 1200 can be based on a design generated by mapping a negative space between segmented anatomic elements of a corrected pathology. The negative space is then filled with a virtual implant. In imbursement-constrained embodiments, the configuration of the negative space can be selected based on one or more parameters for the medical reimbursable virtual implant. For example, the implant 1200 can be a cervical fusion implant, a lumbar fusion implant, an artificial disc, an expandable intervertebral cage, or other implant disclosed herein.

For example, system 100 of FIG. 1 can obtain insurance information for the patient from a database 151. The system 100 can then retrieve one or more design parameters from the database 151 based on the obtained insurance information. The treatment model 181 can then design the patient-specific implant 1200 using the retrieved design parameter(s). The design parameters can be a configuration (e.g., an implant footprint shown as a dashed line in FIG. 12A) for devices approved for use by a regulatory agency or governmental body, payment requirement, reimbursement requirement, etc. Prior to manufacturing the implant 1200, the system can notify the user of the at least one medical reimbursement code for user review and approval.

In the illustrated embodiment, the implant 1200 is a vertebral interbody device having a first (e.g., upper) surface 1202 configured to engage an inferior endplate surface of a superior vertebral body and a second (e.g., lower) surface 1204 configured to engage a superior endplate surface of an inferior vertebral body. The first surface 1202 can have a patient-specific topography designed to match (e.g., mate with) the topography of the inferior endplate surface of the superior vertebral body to form a generally gapless interface therebetween. Likewise, the second surface 1204 can have a patient-specific topography designed to match or mate with the topography of the superior endplate surface of the inferior vertebral body to form a generally gapless interface therebetween. The implant 1200 may also include a recess 1206 or other features configured to promote bony ingrowth. In some embodiments, the implant 1200 has a lattice structure defining a porous upper surface 1210 and a porous lower surface 1212. Characteristics of the lattice structure and/or pores can be selected based on, for example, bone ingrowth rates, threshold target fusion rate, mechanical characteristics of the implant body, etc. The upper surface 1210 and lower surfaces 1212, can be contoured to match the contours of the vertebral endplates, thereby providing a customized fit. In some embodiments, a non-uniform or uniform lattice structure defines upper surface 1210 and lower surfaces 1212, and the porosity of the body, surface 1210, and/or surface 1212 can be in a range of, for example, 40% to 95%, 40% to 90%, 50% to 80%, or other ranges. In some embodiments, the porosity of at least a portion of the body is greater than 30%, 40%, 50%, 60%, 70%, 80%, 90%, or 95%. In some embodiments, the surfaces 1210, 1212 have different porosities for allowing for differential bone ingrowth and/or fusion rates. In some embodiments, the body, surface 1210, surface 1212 has a solid construction without pores.

Because the implant 1200 is patient-specific and designed to induce a geometric change in the patient, the implant 1200 is not necessarily symmetric, and is often asymmetric. For example, in the illustrated embodiment, the implant 1200 has a non-uniform thickness such that a plane defined by the first surface 1202 is not parallel to a central longitudinal axis A of the implant 1200. Of course, because the implants described herein, including the implant 1200, are patient-specific, the present technology is not limited to any particular implant design or characteristic. The implant 1200 can include one or more anchors or screws 1220, 1222 (e.g., bone screws, spinal screws, pedicle screws, facet screws). Additional features of patient-specific implants that can be designed and manufactured in accordance with the present technology are described in U.S. patent application Ser. Nos. 16/987,113 and 17/100,396, the disclosures of which are incorporated by reference herein in their entireties.

Figure 13:
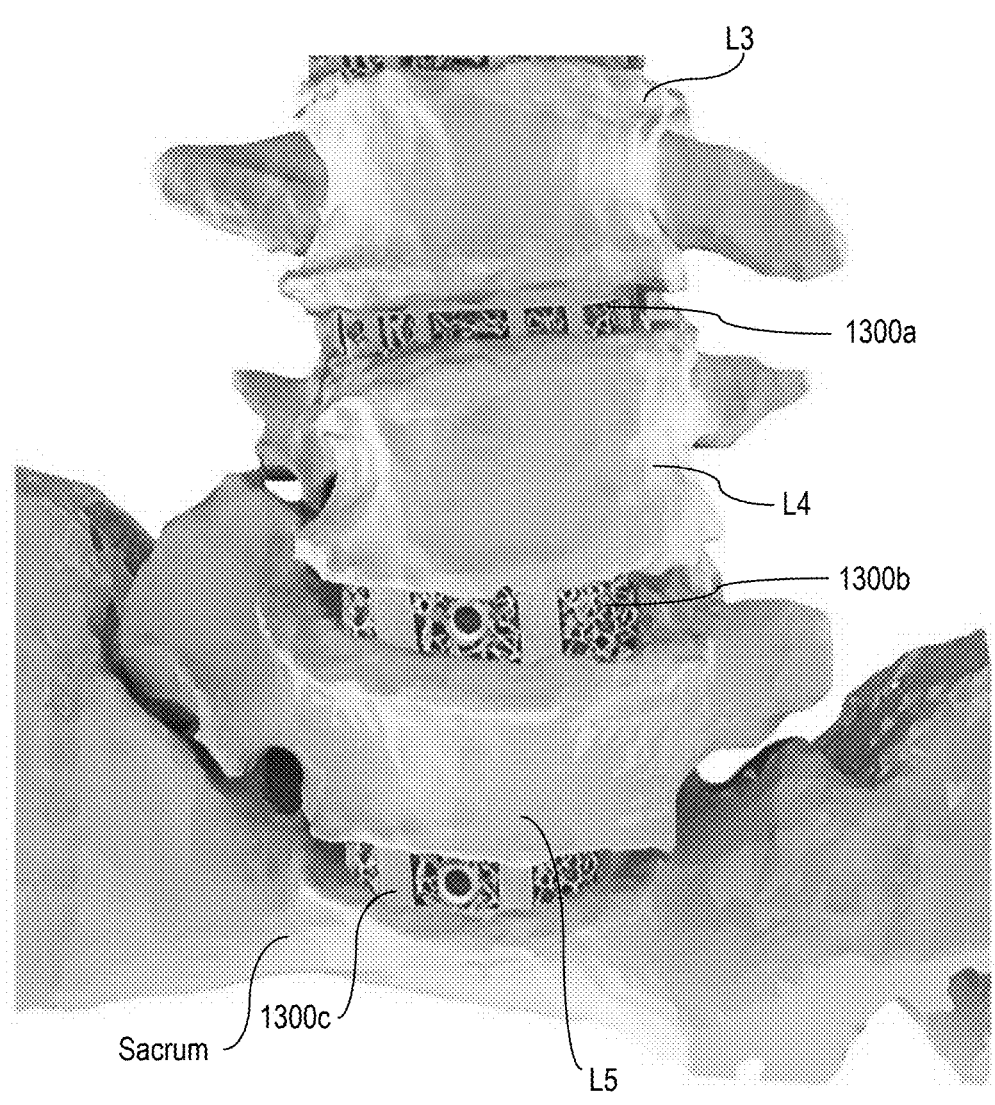
FIG. 13 illustrates a segment of a patient's spine after several patient-specific implants have been implanted therein.

The patient-specific medical procedures described herein can involve implanting more than one patient-specific implant into the patient to achieve the corrected anatomical configuration (e.g., a multi-site procedure). FIG. 13, for example, illustrates a lower spinal cord region having three patient-specific implants 1300a-1300c implanted at different vertebral levels. More specifically, a first implant 1300a is implanted between the L3 and L4 vertebral bodies, a second implant 1300b is implanted between the L4 and L5 vertebral bodies, and a third implant 1300c is implanted between the L5 vertebral body and the sacrum. Together, the implants 1300a-1300c can cause the patient's spinal cord region to assume the previously identified corrected anatomical configuration (e.g., transforming the patient's anatomy from its pre-operative diseased configuration to the post-operative optimized configuration). The implants 1300a-1300c can have lattice structures (e.g., uniform lattice structures, varying lattice structures, etc.) defining a range of porosities, defining solid constructions, or combinations thereof. In some embodiments, more or fewer implants are used to achieve the corrected anatomical configuration. For example, in some embodiments, one, two, four, five, six, seven, eight, or more implants are used to achieve the corrected anatomical configuration. In embodiments involving more than one implant, the implants do not necessarily have the same shape, size, or function. In fact, the multiple implants will often have different geometries and topographies to correspond to the target vertebral level at which they will be implanted. As also shown in FIG. 13, the patient-specific medical procedures described herein can involve treating the patient at multiple target regions (e.g., multiple vertebral levels).

In addition to designing patient-specific medical care based off reference patient data sets, the systems and methods of the present technology may also design patient-specific medical care based off disease progression for a particular patient. In some embodiments, the present technology therefore includes software modules (e.g., machine learning models or other algorithms) that can be used to analyze, predict, and/or model disease progression for a particular patient. The machine learning models can be trained based off a plurality of reference patient data sets that include, in addition to the patient data described with respect to FIG. 1, disease progression metrics for each of the reference patients. The progression metrics can include measurements for disease metrics over a period of time. Suitable metrics may include spinopelvic parameters (e.g., lumbar lordosis, pelvic tilt, sagittal vertical axis (SVA), Cobb angle, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.).

In some embodiments, the present technology includes a disease progression module that includes an algorithm, machine learning model, or other software analytical tool for predicting disease progression in a particular patient. The disease progression module can be trained based on reference patient data sets that include patient information (e.g., age, sex, height, weight, activity level, diet) and disease metrics (e.g., diagnosis, spinopelvic parameters such as lumbar lordosis, pelvic tilt, sagittal vertical axis, Cobb angle, coronal offset, etc., disability scores, functional ability scores, flexibility scores, VAS pain scores, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other healthcare provider, who can review and update the estimate, if necessary.

As a non-limiting example, a particular patient who is a 55-year-old male may have an SVA value of 6 mm. The disease progression module can analyze patient reference data sets to identify disease progression for individual reference patients who have one or more similarities with the particular patient (e.g., individual patients of the reference patients who have an SVA value of about 6 mm and are approximately the same age, weight, height, and/or sex of the patient). Based on this analysis, the disease progression module can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The systems and methods described herein can also generate models/simulations based on the estimated rates of disease progression, thereby modeling different outcomes over a desired period of times. Additionally, the models/simulations can account for any number of additional diseases or condition to predict the patient's overall health, mobility, or the like. These additional diseases or conditions can, in combination with other patient health factors (e.g., height, weight, age, activity level, etc.), be used to generate a patient health score reflecting the overall health of the patient. The patient health score can be displayed for surgeon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physician input for review by the healthcare provider, patient, etc.

In some embodiments, the present technology can also predict, model, and/or simulate disease progression based on one or more potential surgical interventions. For example, the disease progression module may simulate what a patient's anatomy may look like 1, 2, 5, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected disease progression.

Accordingly, in some embodiments, multiple disease progression models (e.g., two, three, four, five, six, or more) are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal intervention can also be fully or semi-automated, as described herein.

Based on the modeled disease progression, the systems and methods described herein can also (i) identify the optimal time for surgical intervention, and/or (ii) identify the optimal type of surgical procedure for the patient. In some embodiments, the present technology therefore includes an intervention timing module that includes an algorithm, machine learning model, or other software analytical tool for determining the optimal time for surgical intervention in a particular patient. This can be done, for example, by analyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module can compare the disease metrics for a particular patient to the reference patient data sets to determine, for similar patients, the point of disease progression at which surgical intervention produced the most favorable outcomes.

As a non-limiting example, the reference patient data sets may include data associated with reference patients' sagittal vertical axis. The data can include (i) sagittal vertical axis values for individual patients over a period of time before surgical intervention (e.g., how fast and to what degree the sagittal vertical axis value changed), (ii) sagittal vertical axis values of the individual patients at the time of surgical intervention, (iii) the change in sagittal vertical axis values after surgical intervention, and (iv) the degree to which the surgical intervention was successful (e.g., based on pain, quality of life, or other factors). Based on the foregoing data, the intervention timing module can, based on a particular patient's sagittal vertical axis value, identify at which point surgical intervention will have the highest likelihood of producing the most favorable outcome. Of course, the foregoing metric is provided by way of example only, and the intervention timing module can incorporate other metrics (e.g., lumbar lordosis, pelvic tilt, sagittal vertical axis, Cobb angle, coronal offset, disability scores, functional ability scores, flexibility scores, VAS pain scores) instead of or in combination with sagittal vertical axis to predict the time at which surgical intervention has the highest probability of providing a favorable outcome for the particular patient.

The intervention timing module may also incorporate one or more mathematical rules based on value thresholds for various disease metrics. For example, the intervention timing module may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a Cobb angle of greater than 10 degrees, and/or a combination of Cobb angle and LL-PI mismatch greater than 20 degrees. Of course, other threshold values and metrics can be used; the foregoing are provided as examples only and in no way limit the present disclosure. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module may provide an estimate for when the patient's metrics will exceed one or more thresholds, thereby providing the patient with an estimate of when surgical intervention may become recommended.

The present technology may also include a treatment planning module that can identify the optimal type of surgical procedure for the patient based on the disease progression of the patient. The treatment planning module can be an algorithm, machine learning model, or other software analytical tool trained or otherwise based on a plurality of reference patient data sets, as previously described. The treatment planning module may also incorporate one or more mathematical rules for identifying surgical procedures. As a non-limiting example, if a LL-PI mismatch is between 10 and 20 degrees, the treatment planning module may recommend an anterior fusion surgery, but if the LL-PI mismatch is greater than 20 degrees, the treatment planning module may recommend both anterior and posterior fusion surgery. As another non-limiting example, if an SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only and in no way limit the present disclosure.

Without being bound by theory, incorporating disease progression modeling into the patient-specific medical procedures described herein may even further increase the effectiveness of the procedures. For example, in many cases it may be disadvantageous operate after a patient's disease progresses to an irreversible or unstable state. However, it may also be disadvantageous to operate too early, before the patient's disease is causing symptoms and/or if the patient's disease may not progress further. The disease progression module and/or the intervention timing module can therefore help identify the window of time during which surgical intervention in a particular patient has the highest probability of providing a favorable outcome for the patient.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A method of manufacturing and implanting a patient-specific interbody cage, the method comprising:
generating a first cage design of a first patient-specific interbody cage configured to be positioned between an upper vertebra and a lower vertebra to achieve a first anatomical correction for a spine of a subject when implanted in the subject, wherein the first patient-specific interbody cage has
an upper contoured porous surface to contact a lower vertebral endplate of the upper vertebra, and
a lower contoured porous surface to contact an upper endplate of the lower vertebra;
performing at least one design check on the first cage design;
in response to determining the first patient-specific interbody cage does not meet a design threshold based on the at least one design check, collecting, via a network connection, third-party data from one or more third-party sources on remote servers;
determining a confidence score for the third-party data based on one or more characteristics of the one or more third-party sources or the third-party data;
in response to the confidence score being above a threshold, selecting one or more parameters from the third-party data; and
generating a second cage design for the first patient-specific interbody cage based on patient data and the one or more parameters from the third-party data; and
after determining the second cage design meets the design threshold,
manufacturing the first patient-specific interbody cage according to the second cage design; and
accessing a disc space between the upper vertebra and the lower vertebra;
implanting the first patient-specific interbody cage at the disc space.
2. The method of example 1, further comprising providing one or more bone screws for anchoring the first patient-specific interbody cage to at least one of the upper vertebra and or the lower vertebra
3. The method of any of examples 1-2, further comprising designing and manufacturing a spinal rod for producing the first anatomical correction.
4. The method of any of examples 1-3, further comprising:
performing a comparison of the third-party data to the patient data;
identifying a subset of the third-party data that is associated with the patient data; and
storing the subset of the third-party data in at least one database for use to generate the second cage design.

5. The method of any of examples 1-4, further comprising:

determining at least one dimension and at least one surface feature of the second cage design based on the one or more parameters of the third-party data; and generating manufacturing instructions for the second cage design with the at least one dimension and the at least one surface feature.

6. A method comprising:

generating a first patient-specific orthopedic implant design based on patient data associated with a patient;

performing at least one design check on the first patient-specific orthopedic implant design;

in response to determining the first patient-specific orthopedic implant design does not meet a design threshold based on the at least one design check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

7. The method of example 6, further comprising:

performing a comparison of the third-party data to the patient data;

identifying a subset of the third-party data that is associated with the patient data; and storing the subset of the third-party data in at least one database.

8. The method of example 6 or example 7, further comprising:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

9. The method of any one of examples 6-8, further comprising:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

10. The method of any one of examples 6-9, further comprising:

integrating the third-party data with the patient data in at least one database;

tagging a first subset of the third-party data associated with the one or more parameters; and removing, from the at least one database, a second subset of the third-party data, wherein the first subset is different from the second subset.

11. The method of any one of examples 6-10, further comprising:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

12. The method of any one of examples 6-11, further comprising:

determining at least one similarity between the patient data and the third-party data; and displaying, via a user interface, the at least one similarity.

13. A system comprising:

one or more processors; and one or more memories storing instructions that, when executed by the one or more processors, cause the system to perform a process comprising:

generating a first patient-specific orthopedic implant design based on patient data associated with a patient;

performing at least one design check on the first patient-specific orthopedic implant design;

in response to determining the first patient-specific orthopedic implant design does not meet a design threshold based on the at least one design check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

14. The system according to example 13, wherein the process further comprises:

performing a comparison of the third-party data to the patient data;

identifying a subset of the third-party data that is associated with the patient data; and storing the subset of the third-party data in at least one database.

15. The system according to example 13 or example 14, wherein the process further comprises:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

16. The system according to any one of examples 13-15, wherein the process further comprises:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

17. The system according to any one of examples 13-16, wherein the process further comprises:

integrating the third-party data with the patient data in at least one database;

tagging a first subset of the third-party data associated with the one or more parameters; and removing, from the at least one database, a second subset of the third-party data, wherein the first subset is different from the second subset.

18. The system according to any one of examples 13-17, wherein the process further comprises:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

19. The system according to any one of examples 13-18, wherein the process further comprises:

determining at least one similarity between the patient data and the third-party data; and displaying, via a user interface, the at least one similarity.

20. A non-transitory computer-readable medium storing instructions that, when executed by a computing system, cause the computing system to perform operations comprising:

generating a first patient-specific orthopedic implant design based on patient data associated with a patient;

performing at least one design check on the first patient-specific orthopedic implant design;

in response to determining the first patient-specific orthopedic implant design does not meet a design threshold based on the at least one design check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

21. The non-transitory computer-readable medium of example 20, wherein the operations further comprise:

performing a comparison of the third-party data to the patient data;

identifying a subset of the third-party data that is associated with the patient data; and storing the subset of the third-party data in at least one database.

22. The non-transitory computer-readable medium of example 20 or example 21, wherein the operations further comprise:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

23. The non-transitory computer-readable medium of any one of examples 20-22, wherein the operations further comprise:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

24. The non-transitory computer-readable medium of any one of examples 20-23, wherein the operations further comprise:

integrating the third-party data with the patient data in at least one database;

tagging a first subset of the third-party data associated with the one or more parameters; and removing, from the at least one database, a second subset of the third-party data, wherein the first subset is different from the second subset.

25. The non-transitory computer-readable medium of any one of examples 20-24, wherein the operations further comprise:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

26. A method comprising:

generating a first patient-specific plan based on patient data associated with a patient;

performing at least one plan check on the first patient-specific plan;

in response to determining the first patient-specific plan does not meet a threshold based on the at least one plan check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific plan based on the patient data and the one or more parameters from the third-party data.

27. The method of example 26, wherein the first patient-specific plan includes at least one of a post-operative anatomical outcome, a patient-specific surgical plan, or an orthopedic implant design, the method further comprising:

performing a comparison of the third-party data to the patient data;

identifying a subset of the third-party data that is associated with the patient data; and storing the subset of the third-party data in at least one database.

28. The method of example 26 or example 27, wherein the first patient-specific plan includes a first orthopedic implant design and the second patient-specific plan includes a second orthopedic implant design, the method further comprising:

determining at least one dimension and at least one surface feature of the second orthopedic implant design based on the one or more parameters of the third-party data; and generating manufacturing instructions for the second orthopedic implant design with the at least one dimension and the at least one surface feature.

29. The method of any one of examples 26-28, further comprising:

training at least one machine learning model to identify at least one trigger for collecting third-party data from the one or more sources;

inputting, into the at least one machine learning model, one or more constraints for a patient-specific implant for the second patient-specific plan; and identifying, by the at least one machine learning model, a subset of the third-party data that complies with the one or more constraints.

30. The method of any one of examples 26-29, further comprising:

integrating the third-party data with the patient data in at least one database;

tagging a first subset of the third-party data associated with the one or more parameters; and removing, from the at least one database, a second subset of the third-party data, wherein the first subset is different from the second subset.

31. The method of any one of examples 26-30, further comprising:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

32. The method of any one of examples 26-31, further comprising:

determining at least one similarity between the patient data and the third-party data; and displaying, via a user interface, the at least one similarity.

33. A system comprising:

one or more processors; and one or more memories storing instructions that, when executed by the one or more processors, cause the system to perform a process comprising:

generating a first patient-specific plan based on patient data associated with a patient;

performing at least one plan check on the first patient-specific plan;

in response to determining the first patient-specific plan does not meet a design threshold based on the at least one plan check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific plan based on the patient data and the one or more parameters from the third-party data.

34. The system according to example 33, wherein the first patient-specific plan includes at least one of a post-operative anatomical outcome, a patient-specific surgical plan, or an orthopedic implant design, wherein the process further comprises:

performing a comparison of the third-party data to the patient data;

identifying a subset of the third-party data that is associated with the patient data; and storing the subset of the third-party data in at least one database.

35. The system according to example 33 or example 34, wherein the first patient-specific plan includes a first orthopedic implant design and the second patient-specific plan includes a second orthopedic implant design, wherein the process further comprises:

determining at least one dimension and at least one surface feature of the second orthopedic implant design based on the one or more parameters of the third-party data; and generating manufacturing instructions for the second orthopedic implant design with the at least one dimension and the at least one surface feature.

36. The system according to any one of examples 33-35, wherein the process further comprises:

training at least one machine learning model to identify at least one trigger for collecting third-party data from the one or more sources;

inputting, into the at least one machine learning model, one or more design constraints for a patient-specific implant for the second patient-specific plan; and identifying, by the at least one machine learning model, a subset of the third-party data that complies with the one or more design constraints.

37. The system according to any one of examples 33-36, wherein the process further comprises:

integrating the third-party data with the patient data in at least one database;

tagging a first subset of the third-party data associated with the one or more parameters; and removing, from the at least one database, a second subset of the third-party data, wherein the first subset is different from the second subset.

38. The system according to any one of examples 33-37, wherein the process further comprises:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

39. The system according to any one of examples 33-38, wherein the process further comprises:

determining at least one similarity between the patient data and the third-party data; and displaying, via a user interface, the at least one similarity.

40. A non-transitory computer-readable medium storing instructions that, when executed by a computing system, cause the computing system to perform operations comprising:

generating a first patient-specific plan based on patient data associated with a patient;

performing at least one plan check on the first patient-specific plan;

in response to determining the first patient-specific plan does not meet a design threshold based on the at least one plan check, collecting, via a network connection, third-party data from one or more third-party sources on remote servers;

determining a confidence score for the third-party data based on one or more characteristics of one or more sources or the third-party data;

in response to the confidence score being above a threshold, selecting one or more parameters from the third-party data; and generating a second patient-specific plan based on the patient data and the one or more parameters from the third-party data.

41. The non-transitory computer-readable medium of example 40, wherein the first patient-specific plan includes at least one of a post-operative anatomical outcome, a patient-specific surgical plan, or an orthopedic implant design, wherein the operations further comprise:

performing a comparison of the third-party data to the patient data;

identifying a subset of the third-party data that is associated with the patient data; and storing the subset of the third-party data in at least one database.

42. The non-transitory computer-readable medium of example 40 or example 41, wherein the first patient-specific plan includes a first orthopedic implant design and the second patient-specific plan includes a second orthopedic implant design, wherein the operations further comprise:

determining at least one dimension and at least one surface feature of the second orthopedic implant design based on the one or more parameters of the third-party data; and generating manufacturing instructions for the second orthopedic implant design with the at least one dimension and the at least one surface feature.

43. The non-transitory computer-readable medium of any one of examples 40-42, wherein the operations further comprise:

training at least one machine learning model to identify at least one trigger for collecting third-party data from the one or more sources;

inputting, into the at least one machine learning model, one or more design constraints for a patient-specific implant for the second patient-specific plan; and identifying, by the at least one machine learning model, a subset of the third-party data that complies with the one or more design constraints.

44. The non-transitory computer-readable medium of any one of examples 40-43, wherein the operations further comprise:

integrating the third-party data with the patient data in at least one database;

tagging a first subset of the third-party data associated with the one or more parameters; and removing, from the at least one database, a second subset of the third-party data, wherein the first subset is different from the second subset.

45. The non-transitory computer-readable medium of any one of examples 40-44, wherein the operations further comprise:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically malleable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. Application No. 63/657,725, filed on Jun. 7, 2024, titled "PATIENT-SPECIFIC IMPLANT DESIGN AND PLATFORM WITH CLINICAL DATA ACQUISITION";

U.S. application Ser. No. 16/048,167, filed on Jul. 27, 2017, titled "SYSTEMS AND METHODS FOR ASSISTING AND AUGMENTING SURGICAL PROCEDURES";

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";

U.S. application Ser. No. 16/207,116, filed on Dec. 1, 2018, titled "SYSTEMS AND METHODS FOR MULTI-PLANAR ORTHOPEDIC ALIGNMENT";

U.S. application Ser. No. 16/352,699, filed on Mar. 13, 2019, titled "SYSTEMS AND METHODS FOR ORTHOPEDIC IMPLANT FIXATION";

U.S. application Ser. No. 16/383,215, filed on Apr. 12, 2019, titled "SYSTEMS AND METHODS FOR ORTHOPEDIC IMPLANT FIXATION";

U.S. application Ser. No. 16/569,494, filed on Sep. 12, 2019, titled "SYSTEMS AND METHODS FOR ORTHOPEDIC IMPLANTS";

U.S. Application No. 62/773,127, filed on Nov. 29, 2018, titled "SYSTEMS AND METHODS FOR ORTHOPEDIC IMPLANTS";

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";

U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS";

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS";

U.S. application Ser. No. 17/100,396, filed Nov. 20, 2020, titled "PATIENT-SPECIFIC VERTEBRAL IMPLANTS WITH POSITIONING FEATURES";

U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS";

U.S. application Ser. No. 17/868,729, filed Jul. 19, 2022, titled "SYSTEMS FOR PREDICTING INTRAOP-

ERATIVE PATIENT MOBILITY AND IDENTIFYING MOBILITY-RELATED SURGICAL STEPS";

U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES";

International Application No. PCT/US2021/012065, filed Jan. 4, 2021, titled "PATIENT-SPECIFIC MEDICAL PROCEDURES AND DEVICES, AND ASSOCIATED SYSTEMS AND METHODS";

International Patent Application No. PCT/US22/48729, filed Nov. 2, 2022, titled "PATIENT-SPECIFIC ARTHROPLASTY DEVICES AND ASSOCIATED SYSTEMS AND METHODS";

U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS";

U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA";

International Patent Application No. PCT/US22/48729, filed Nov. 2, 2022, titled "PATIENT-SPECIFIC ARTHROPLASTY DEVICES AND ASSOCIATED SYSTEMS AND METHODS";

U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS"; and U.S. Pat. No. 11,793,577, issued Oct. 24, 2023, titled "TECHNIQUES TO MAP THREE-DIMENSIONAL

HUMAN ANATOMY DATA TO TWO-DIMENSIONAL HUMAN ANATOMY DATA."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter. The patient can be a human patient, such as an adult human patient, teenager human patient, child human patient, etc.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method of manufacturing and implanting a patient-specific interbody cage, the method comprising:

generating a first cage design of a first patient-specific interbody cage configured to be positioned between an upper vertebra and a lower vertebra to achieve a first anatomical correction for a spine of a subject when implanted in the subject, wherein the first patient-specific interbody cage has an upper contoured porous surface to contact a lower vertebral endplate of the upper vertebra, and a lower contoured porous surface to contact an upper endplate of the lower vertebra;

performing at least one design check on the first cage design;

determining patient data of the subject includes at least one edge case pathology based on the at least one design check;

in response to determining the patient data includes the at least one edge case pathology, collecting, via a network connection, third-party data from one or more third-party sources on remote servers, wherein the third-party data is associated with the at least one edge case pathology;

determining a confidence score for the third-party data based on one or more characteristics of the one or more third-party sources or the third-party data;

in response to the confidence score being above a threshold, selecting one or more parameters from the third-party data; and generating a second cage design for the first patient-specific interbody cage based on the patient data and the one or more parameters from the third-party data; and after determining the second cage design meets a design threshold, manufacturing the first patient-specific interbody cage according to the second cage design; and accessing a disc space between the upper vertebra and the lower vertebra;

implanting the first patient-specific interbody cage at the disc space.

2. The method of claim 1, further comprising providing one or more bone screws for anchoring the first patient-specific interbody cage to at least one of the upper vertebra and or the lower vertebra.

3. The method of claim 1, further comprising designing and manufacturing a spinal rod for producing the first anatomical correction.

4. The method of claim 1, further comprising:

performing a comparison of the third-party data to the patient data;

identifying a subset of the third-party data that is associated with the patient data;

and storing the subset of the third-party data in at least one database for use to generate the second cage design.

5. The method of claim 1, further comprising:

determining at least one dimension and at least one surface feature of the second cage design based on the one or more parameters of the third-party data; and generating manufacturing instructions for the second cage design with the at least one dimension and the at least one surface feature.

6. A method comprising:

generating a first patient-specific orthopedic implant design based on patient data associated with a patient;

performing at least one design check on the first patient-specific orthopedic implant design;

determining the patient data includes at least one edge case pathology based on the at least one design check;

in response to determining the patient data includes the at least one edge case pathology, collecting, via a network connection, third-party data from one or more third-party sources on remote servers, wherein the third-party data is associated with the at least one edge case pathology;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

7. The method of claim 6, further comprising:

performing a comparison of the third-party data to the patient data;

identifying a subset of the third-party data that is associated with the patient data; and storing the subset of the third-party data in at least one database.

8. The method of claim 6, further comprising:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

9. The method of claim 6, further comprising:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

10. The method of claim 6, further comprising:

integrating the third-party data with the patient data in at least one database;

tagging a first subset of the third-party data associated with the one or more parameters; and removing, from the at least one database, a second subset of the third-party data, wherein the first subset is different from the second subset.

11. The method of claim 6, further comprising:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

12. The method of claim 6, further comprising:

determining at least one similarity between the patient data and the third-party data; and displaying, via a user interface, the at least one similarity.

13. A system comprising:

one or more processors; and one or more memories storing instructions that, when executed by the one or more processors, cause the system to perform a process comprising:

generating a first patient-specific orthopedic implant design based on patient data associated with a patient;

performing at least one design check on the first patient-specific orthopedic implant design;

determining the patient data includes at least one edge case pathology based on the at least one design check;

in response to determining the patient data includes the at least one edge case pathology, collecting, via a network connection, third-party data from one or more third-party sources on remote servers, wherein the third-party data is associated with the at least one edge case pathology;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

14. The system according to claim 13, wherein the process further comprises:

performing a comparison of the third-party data to the patient data;

identifying a subset of the third-party data that is associated with the patient data; and storing the subset of the third-party data in at least one database.

15. The system according to claim 13, wherein the process further comprises:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

16. The system according to claim 13, wherein the process further comprises:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

17. The system according to claim 13, wherein the process further comprises:

integrating the third-party data with the patient data in at least one database;

tagging a first subset of the third-party data associated with the one or more parameters; and removing, from the at least one database, a second subset of the third-party data, wherein the first subset is different from the second subset.

18. The system according to claim 13, wherein the process further comprises:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

19. The system according to claim 13, wherein the process further comprises:

determining at least one similarity between the patient data and the third-party data; and displaying, via a user interface, the at least one similarity.

20. A non-transitory computer-readable medium storing instructions that, when executed by a computing system, cause the computing system to perform operations comprising:

generating a first patient-specific orthopedic implant design based on patient data associated with a patient;

performing at least one design check on the first patient-specific orthopedic implant design;

determining the patient data includes at least one edge case pathology based on the at least one design check;

in response to determining the patient data includes the at least one edge case pathology, collecting, via a network connection, third-party data from one or more third-party sources on remote servers, wherein the third-party data is associated with the at least one edge case pathology;

determining a confidence score for the third-party data based on one or more characteristics of one or more sources or the third-party data;

in response to the confidence score being above a threshold, selecting one or more parameters from the third-party data; and generating a second patient-specific orthopedic implant design based on the patient data and the one or more parameters from the third-party data.

21. The non-transitory computer-readable medium of claim 20, wherein the operations further comprise:

performing a comparison of the third-party data to the patient data;

identifying a subset of the third-party data that is associated with the patient data; and storing the subset of the third-party data in at least one database.

22. The non-transitory computer-readable medium of claim 20, wherein the operations further comprise:

determining at least one dimension and at least one surface feature of the second patient-specific orthopedic implant design based on the one or more parameters of the third-party data; and generating manufacturing instructions for the second patient-specific orthopedic implant design with the at least one dimension and the at least one surface feature.

23. The non-transitory computer-readable medium of claim 20, wherein the operations further comprise:

training at least one machine learning model to identify at least one trigger for collecting third-party data from the one or more sources;

inputting, into the at least one machine learning model, one or more design constraints for a patient-specific implant; and identifying, by the at least one machine learning model, a subset of the third-party data that complies with the one or more design constraints.

24. The non-transitory computer-readable medium of claim 20, wherein the operations further comprise:

integrating the third-party data with the patient data in at least one database;

tagging a first subset of the third-party data associated with the one or more parameters; and removing, from the at least one database, a second subset of the third-party data, wherein the first subset is different from the second subset.

25. The non-transitory computer-readable medium of claim 20, wherein the operations further comprise:

identifying at least one trigger to collect the third-party data from the one or more sources;

determining a subset of the third-party data associated with the patient data based on at least one of: an anatomical feature of the patient, a demographic of the patient, and an activity level of the patient; and sending a notification to a user regarding the subset of the third-party data, wherein the notification includes one or more links to the subset of the third-party data.

26. A computer-implemented method comprising:

determining patient data associated with a patient includes at least one edge case pathology;

in response to determining the patient data includes the at least one edge case pathology, collecting, via a network connection, third-party data from one or more third-party sources on remote servers, wherein the third-party data is associated with the at least one edge case pathology;

determining a confidence score for the third-party data based on one or more characteristics of at least one of the one or more third-party sources, or the third-party data; and in response to the confidence score being above a threshold, generating a three-dimensional patient-specific orthopedic implant design based on the patient data and the third-party data.

27. The computer-implemented method of claim 26, further comprising:

generating, based on the third-party data, a surgical plan for implanting an implant manufactured according to the patient-specific orthopedic implant design.

28. The computer-implemented method of claim 26, further comprising:

generating a three-dimensional virtual anatomical model that represents a planned corrected spinal anatomy for the patient, wherein the planned corrected spinal anatomy is based on the third party data, and generating a virtual implant model using the three-dimensional virtual anatomical model for achieving the planned corrected spinal anatomy.

29. The computer-implemented method of claim 28, further comprising generating a three-dimensional patient-specific orthopedic implant design based on the virtual implant model, wherein the three-dimensional patient-specific orthopedic implant design is configured to be used by a machine to manufacture a patient-specific orthopedic implant for the patient.

* * * * *